US005935570A

United States Patent [19]

Koprowski et al.

[11] Patent Number: 5,935,570

[45] Date of Patent: Aug. 10, 1999

[54] SYNTHESIS OF IMMUNOLOGIC, THERAPEUTIC AND PROPHYLACTIC COMPOUNDS BY TRANSFORMED CLAVIBACTER

[75] Inventors: Hilary Koprowski, Wynnewood, Pa.; Peter Spikins Carlson, Alexandria, Va.; Douglas Craig Hooper, Medford, N.J.; Laura Jane Conway, Haverford; Frank H. Michaels, Havertown, both of Pa.; Anna Modelska, Wynnewood, Pa.; Zhen Fang Fu, Cherry Hill, N.J.

[73] Assignee: Thomas Jefferson University, Philadelphia, Pa.

[21] Appl. No.: 08/546,117

[22] Filed: Oct. 20, 1995

[51] Int. Cl.[6] .......................... A01H 4/00; A61K 39/00; C07K 14/00; C12N 5/04

[52] U.S. Cl. .................. 424/93.4; 424/93.2; 424/93.461; 424/184.1; 424/224.1; 435/69.1; 435/69.3; 435/172.1; 435/71.1; 435/71.2; 435/410; 435/419; 435/252.3; 530/350; 536/23.7; 800/279; 800/288; 800/298

[58] Field of Search .......................... 424/192.4, 93.461, 424/93.4, 184.1, 224.1, 93.2; 435/69.1, 69.3, 172.1, 71.1, 71.2, 410, 419, 252.3; 530/350; 536/23.7; 800/279, 288, 298

[56] References Cited

U.S. PATENT DOCUMENTS

| | | | |
|---|---|---|---|
| 5,415,672 | 5/1995 | Fahey et al. | 47/57.6 |
| 5,446,127 | 8/1995 | Garcia-Olmedo et al. | 530/300 |
| 5,468,483 | 11/1995 | Thompson et al. | 424/93.461 |
| 5,580,852 | 12/1996 | Putnam et al. | 514/2 |
| 5,588,862 | 12/1996 | Corbin et al. . | |
| 5,612,487 | 3/1997 | Lam et al. | 800/205 |

FOREIGN PATENT DOCUMENTS

| | | | |
|---|---|---|---|
| 0125468 | 11/1984 | European Pat. Off. | C12N 15/00 |
| 0 502 719 | 9/1992 | European Pat. Off. | A01N 63/00 |
| WO8703303 | 6/1987 | WIPO | C12N 15/00 |
| WO9110363 | 7/1991 | WIPO | A01N 63/00 |
| WO9420135 | 9/1994 | WIPO | A61K 39/00 |
| WO9420604 | 9/1994 | WIPO . | |

OTHER PUBLICATIONS

Moffat Science 268:659–660, Exploring Transgenic Plants as a New Vaccine Source, 1995.

International Search Report, International Application No. PCT/US96/16638.

Lampel et al Applied & Environmental Microbiology 60:501–508, 1994.

Cárdenas et al., “Oral Immunization Using Live Attenuated Salmonella spp. as Carriers of Foreign Antigens,” Clinical Microbiology Reviews, pp. 328–342 (1992).

Carrier et al., “Expression of Human IL–1β in *Salmonella typhimurium* A Model System for the Delivery of Recombinant Therapeutic Proteins in Vivo,” The Journal of Immunology, vol. 148, pp. 1176–1181 (1992).

Charles et al., “Gene Expression and the Development of Live Enteric Vaccines,” TIBTECH, pp. 117–121 (1990).

Doggett et al., “Immune Responses to *Streptococcus sobrinus* Surface Protein Antigen A Expressed by Recombinant *Salmonella typhimurium*,” Infection and Immunity, vol. 61, pp. 1859–1866 (1995).

Medical Application, “Exploring Transgenic Plants as a New Vaccine Source,” Science, vol. 268, pp. 658–660 (May, 1995).

Zhen Fang Fu et al., “Rabies virus nucleoprotein expressed in and purified from insect cells is efficacious as a vaccine,” Proc. Natl. Acad. Sci., vol. 88, pp. 2001–2005 (1991).

Zhen Fang Fu et al., “Oral vaccination of raccoons (*Procyon lotor*) with baculovirus–expressed rabies virus glycoprotein,” Vaccine, vol. 11, pp. 925–928 (1993).

Haq et al., “Oral Immunization with a Recombinant Bacterial Antigen Produced in Transgenic Plants,” Science, vol. 268, pp. 714–716 (1995).

Ianaro et al., “Expression of TGF–β in attenuated *Salmonella typhimurium*: oral administration leads to the reduction of inflammation, IL–2 and IFN–γ, but enhancement of IL–10 in carrageenin–induced oedema in mice,” University of Glasgow, pp. 8–15 (1994).

Crop Genetics International, “InCide™ Biopesticides Technical Manual,” pp. 1–11.

Kraehenbuhl et al., “Molecular and Cellular Basis of Immune Protection of Mucosal Surfaces,” Physiological Reviews, vol. 72, pp. 853–879 (1992).

Curtiss III, et al., “Selective Delivery of Antigens by Recombinant Bacteria,” New Strategies for Oral Immunization, pp. 35–49 (1989).

Warren E. Leary, The New York Times, America Online:M-HandP, pp. 1–3 (1995).

Medaglini et al., “Mucosal and systemic immune responses to a recombinant protein expressed on the surface of the oral commensal bacterium *Streptococcus gordonii* after oral colonization,” Proc. Natl. Acad. Sci., vol. 92, pp. 6868–6872 (1995).

Pozzi et al., “Delivery and Expression of a Heterologous Antigen on the Surface of Streptococci,” Infection and Immunity, vol. 60, pp. 1902–1907 (1992).

Research News, “Triggering the First Line of Defense,” Science, vol. 265, pp. 1522–1524 (1994).

Tacket et al., “Comparison of the Safety and Immunogenicity of ΔarocC ΔaroD and Δcya Δcrp *Salmonella typhi* Strains in Adult Volunteers,” Infection and Immunity, vol. 60, pp. 536–541 (1992).

(List continued on next page.)

*Primary Examiner*—James C. Housel
*Assistant Examiner*—Phuong T. Bui
*Attorney, Agent, or Firm*—Volpe and Koenig, P.C.

[57] ABSTRACT

A process for the synthesis and delivery of bioactive compounds, compounds that have a therapeutic, biochemical, or immunologic, effect on an animal, such as human. In the process, clavibacter is genetically altered so that it synthesizes the bioactive compound. A plant may be infected with the genetically altered clavibacter and used an as oral delivery system.

18 Claims, 15 Drawing Sheets

OTHER PUBLICATIONS

Turner et al., "Endophytes: An Alternative Genome for Crop Improvement," International Crop Science I. (1993) Crop Science Society of America, Madison, WI.

Thanavala et al., "Immunogenicity of transgenic plant–derived hepatitis B surface antigen," Proc. Natl. Acad. Sci., vol. 92, pp. 3358–3361 (Apr., 1995).

Steven C. Witt, "Case Study: Crop Genetics International," Biotechnology, Microbes and the Environment, Briefbook, pp. 63–85 (1990).

Fig. 10

ATGGATGCCGACAAGATTGTATTCAAAGTCAATAATCAGG 40
TGGTCTCTTTGAAGCCTGAGATTATCGTGGATCAACATGA 80
GTACAAGTACCCTGCCATCAAAGATTTGAAAAAGCCCTGT 120
ATAACCCTAGGAAAGGCTCCCGATTTAAATAAAGCATACA 160
AGTCAGTTTTGTCAGGCATGAGCGCCGCCAAACTTGATCC 200

TGACGATGTATGTTCCTATTTGGCAGCGGCAATGCAGTTT 240
TTTGAGGGGACATGTCCGGAAGACTGGACCAGCTATGGAA 280
TCGTGATTGCACGAAAAGGAGATAAGATCACCCCAGGTTC 320
TCTGGTGGAGATAAAACGTACTGATGTAGAAGGGAATTGG 360
GCTCTGACAGGAGGCATGGAACTGACAAGAGACCCCACTG 400

TCCCTGAGCATGCGTCCTTAGTCGGTCTTCTCTTGAGTCT 440
GTATAGGTTGAGCAAAATATCCGGGCAAAACACTGGTAAC 480
TATAAGACAAACATTGCAGACAGGATAGAGCAGATTTTTG 520
AGACAGCCCCTTTTGTTAAAATCGTGGAACACCATACTCT 560
AATGACAACTCACAAAATGTGTGCTAATTGGAGTACTATA 600

CCAAACTTCAGATTTTTGGCCGGAACCTATGACATGTTTT 640
TCTCCCGGATTGAGCATCTATATTCAGCAATCAGAGTGGG 680
CACAGTTGTCACTGCTTATGAAGACTGTTCAGGACTGGTA 720
TCATTTACTGGGTTCATAAAACAAATCAATCTCACCGTTA 760
GAGAGGCAATACTATATTTCTTCCACAAGAACTTTGAGGA 800

AGAGATAAGAAGAATGTTTGAGCCAGGCCAGGAGACAGCT 840
GTTCCTCACTCTTATTTCATCCACTTCCGTTCACTAGGCT 880
TGAGTGGGAAATCTCCTTATTCATCAAATGCTGTTGGTCA 920
CGTGTTCAATCTCATTCACTTTGTAGGATGCTATATGGGT 960
CAAGTCAGATCCCTAAATGCAACGGTTATTGCTGCATGTG 1000

CTCCTCATGAAATGTCTGTTCTAGGGGGCTATCTGGGAGA 1040
GGAATTCTTCGGGAAAGGGACATTTGAAAGAAGATTCTTC 1080
AGAGATGAGAAAGAACTTCAAGAATACGAGGCGGCTGAAC 1120
TGACAAAGACTGACGTAGCACTGGCAGATGATGGAACTGT 1160
CAACTCTGACGACGAGGACTACTTCTCAGGTGAAACCAGA 1200

AGTCCGGAGGCTGTTTATACTCGAATCATGATGAATGGAG 1240
GTCGACTGAAGAGATCTCACATACGGAGATATGTCTCAGT 1280
CAGTTCCAATCATCAAGCCCGTCCAAACTCATTCGCCGAG 1320
TTTCTAAACAAGACATATTCGAGTGACTCATAAGAAG 1357

Fig. 12
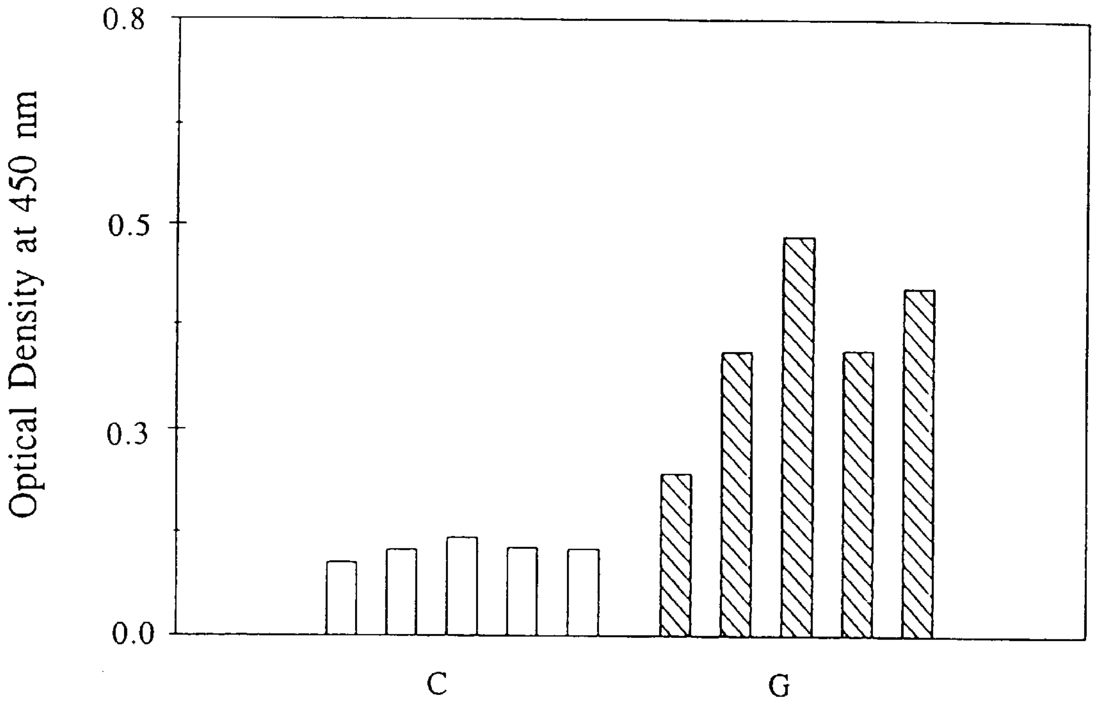
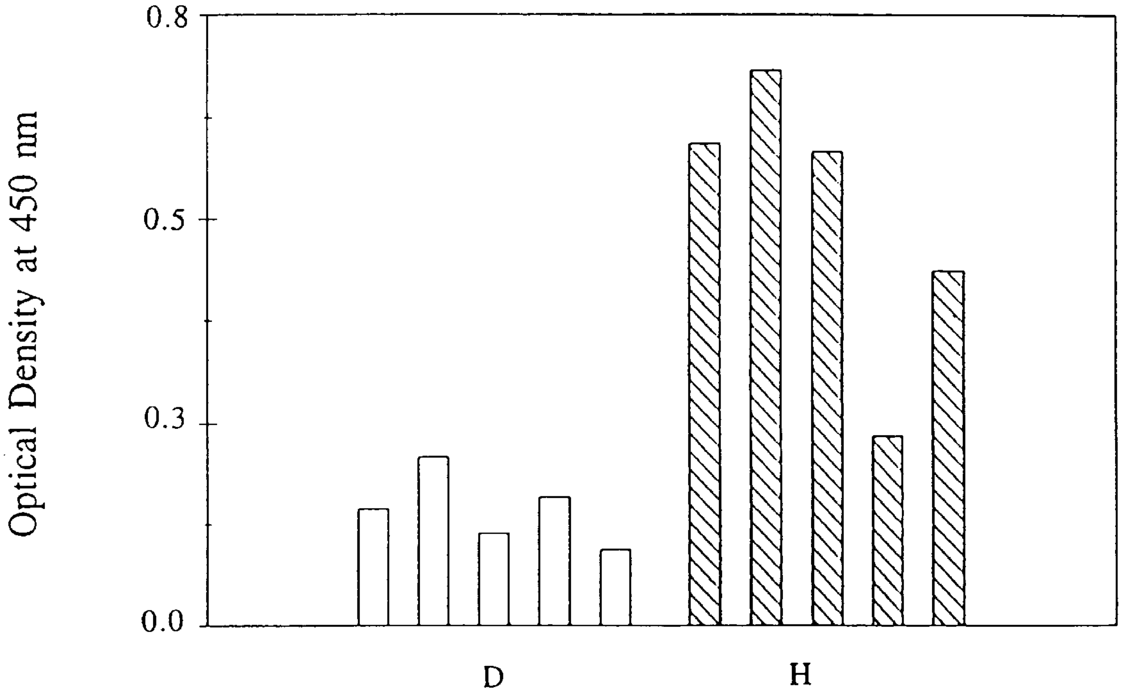

Fig. 13
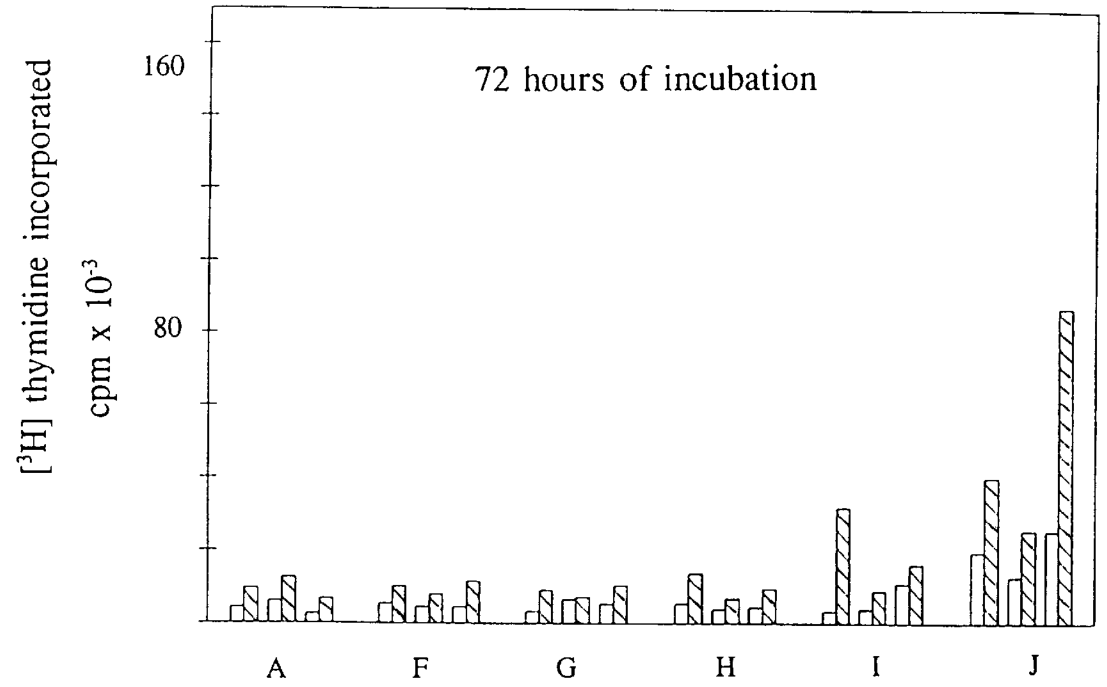
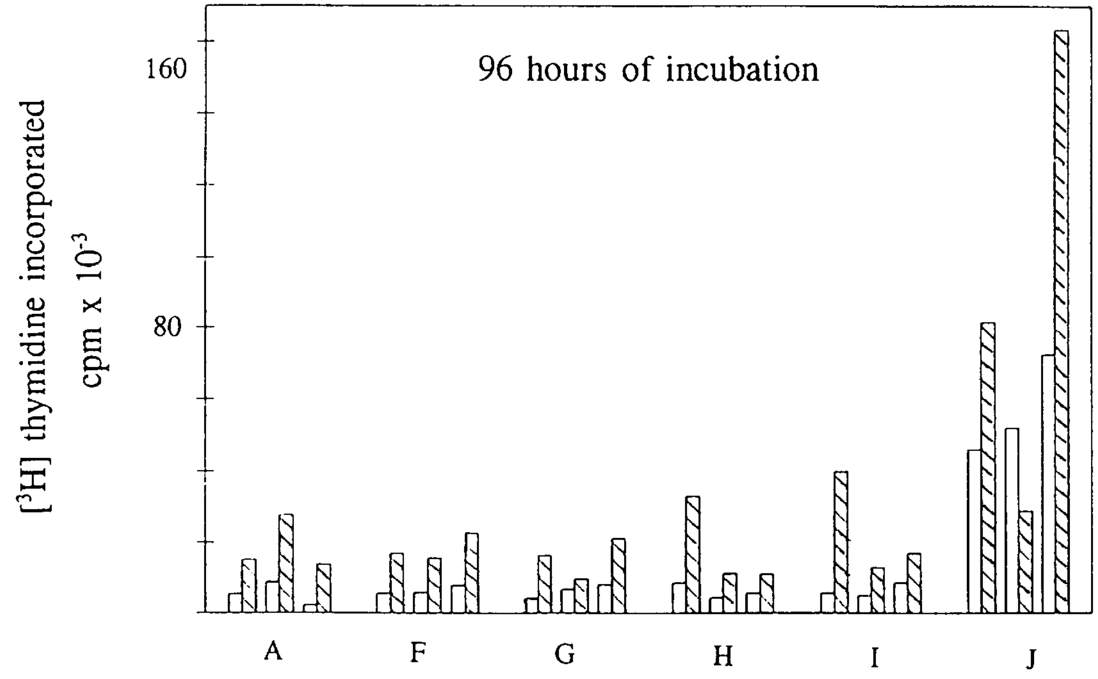

SYNTHESIS OF IMMUNOLOGIC, THERAPEUTIC AND PROPHYLACTIC COMPOUNDS BY TRANSFORMED CLAVIBACTER

FIELD OF THE INVENTION

The invention relates to the synthesis of immunologic, therapeutic, and prophylactic compounds by endophytic microorganisms.

BACKGROUND

Plants and microorganisms may be modified to produce bioactive compounds of medical interest. When the plant or microorganism is edible, it is potentially both the site of synthesis and the vehicle for delivering the bioactive compound. Such a synthesis-delivery system can be relatively inexpensive and free of the pathogens that may be associated with the cultured animal cells used in conventional vaccine and therapeutic compound production methods. Plant and non-plant systems that have been proposed for either vaccine or therapeutic compound production or such production and delivery include:

1) Plants whose genetic material has been transformed;
2) Plants infected with genetically modified plant viruses;
3) Genetically altered and attenuated pathogenic microorganisms; and
4) Genetically altered commensal microorganisms.

To be of value, however, the modified plant or microorganism must be capable of synthesizing the vaccine or therapeutic compound of interest in quantities sufficient to generate a meaningful biological response. Additionally, the vaccine or therapeutic compound, if administered by the oral route, must not be degraded in the digestive tract of the treated animal subject. However, only genetically altered microbial mammalian pathogens have been shown to induce an immune response or effective immune protection against a mucosal pathogen.

Microorganisms have a potential advantage as a medically useful compound delivery vehicle, as compared to genetically transformed or virus-infected plants, in that microorganisms have a well characterized, malleable genetic system for synthesis of the bioactive compound. As a result, genetic manipulation of the microorganism is more readily accomplished than that of the plant. On the other hand, attenuated pathogenic microorganisms engineered to deliver medically useful compounds carry a constant risk of reversion or transformation to the virulent state; even the perception of that risk is a hindrance to the commercial use of such systems. Similarly, genetic manipulation of commensal microorganisms, which by definition already have the ability to survive in their human or other animal host, carries the risk that the ability to live symbiotically with the host may be destroyed and, furthermore, growth or other properties detrimental to the host may be acquired.

The present invention utilizes plants infected with genetically modified endophytic microorganisms as the vehicle for therapeutic or prophylactic compound synthesis and delivery. In some embodiments of the invention, the microorganism is propagated inside a plant, so that the plant becomes the delivery vehicle for the genetically modified microorganism and the compound. Until the present invention, plants had been infected with genetically modified endophytic microorganisms only for purposes of synthesizing pesticides in the plant, thereby eliminating the need for spraying the plant with conventional organic chemical or biological pesticides potentially harmful to humans and animals.

BRIEF SUMMARY OF THE INVENTION

The present invention, in one general aspect, is a process for the synthesis and delivery of bioactive compounds, compounds that have a therapeutic, biochemical, or immunologic, effect on an animal, such as human. In the process, an endophytic microorganism (bacteria or fungus) is genetically altered so that it synthesizes the bioactive compound. In an embodiment of interest, a plant infected with the genetically altered microorganism is used as an oral delivery system.

BRIEF DESCRIPTION OF THE DRAWINGS

FIG. 10 Nucleotide sequence of the rabies nucleoprotein gene (SEQ ID NO:8).

FIG. 12. Mucosal response to BT after feeding Cxc-BT by gastric intubation as indicated by amount of BT-specific IgA. The five open histograms in the “C” group are for five mice, each immunized with $5\times10^5$ cfu of Cxc. The five cross-hatched histograms in the “G” group are for five mice, each immunized with $5\times10^5$ cfu of Cxc-BT. The five open histograms in the “D” group are for five mice, each immunized with $5\times10^7$ cfu of Cxc. The five cross-hatched histograms in the “H” group are for five mice, each immunized with $5\times10^7$ cfu of Cxc-BT.

FIG. 13. BT-specific proliferative response of spleen T cells from mice immunized 4× using gastric intubation. Cross-hatched histograms: Cxc-BT is added to the assay. Open histograms: Sucrose free of Cxc-BT is added to the assay. At each time of incubation (72 hours or 96 hours), the three pairs of histograms in the “A” group are for three control mice, those fed sucrose free of Cxc by gastric intubation. At each time of incubation, the three pairs of histograms in the “F” group are for three mice immunized with $5\times10^3$ cfu Cxc-BT via gastric intubation, the three pairs of histograms in the “G” group are for three mice immunized with $5\times10^5$ cfu Cxc-BT via gastric intubation, the three pairs of histograms in the “H” group are for three mice immunized with $5\times10^7$ cfu via Cxc-BT gastric intubation, the three pairs of histograms in the “I” group are for three mice immunized with $5\times10^9$ cfu Cxc-BT via gastric intubation and the three pairs of histograms in the “J” group are for three mice immunized with $5\times10^9$ cfu Cxc-BT via i.p. injection.

DETAILED DESCRIPTION

Glossary and Discussion of Terms Used

Figure 1:
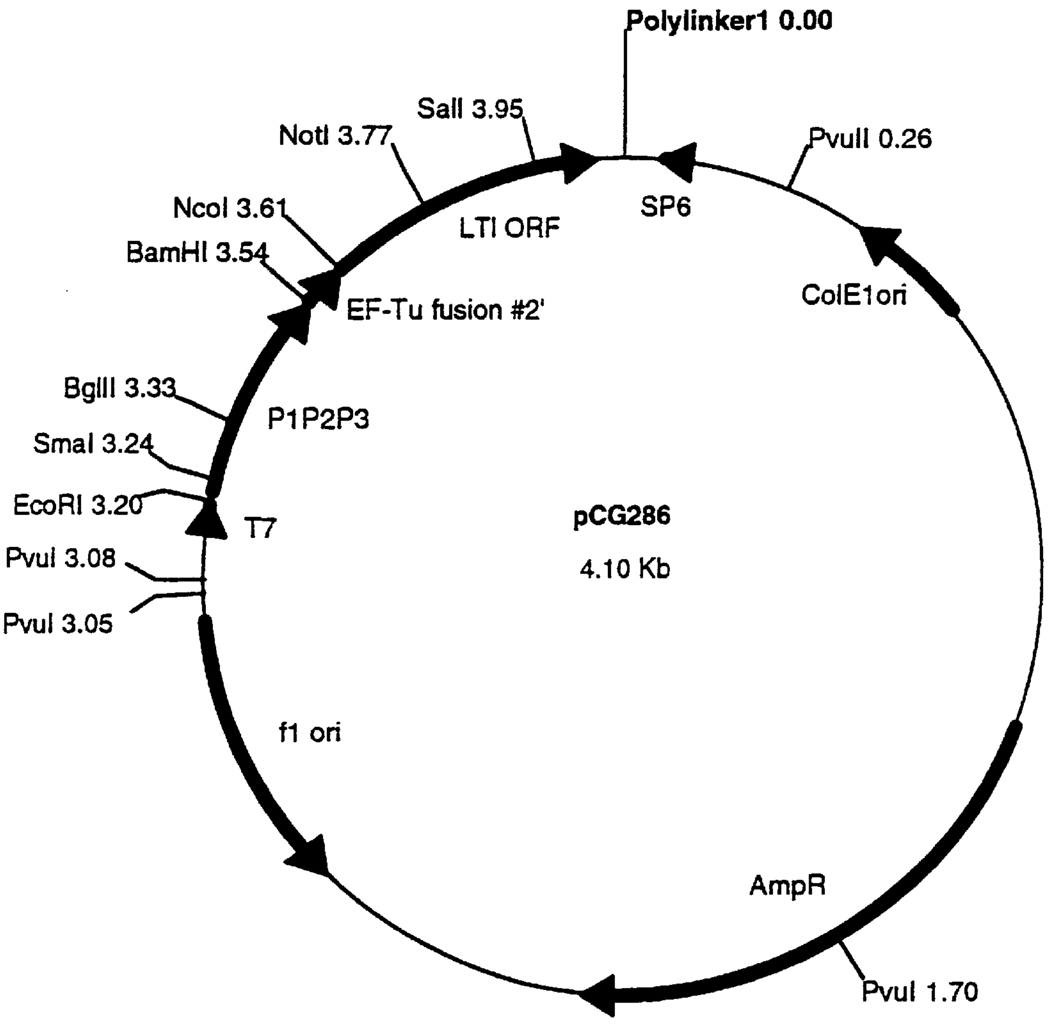
FIG. 1. Map of plasmid pCG286.

An "animal" is any multicellular organism, including humans, of the kingdom Animalia. Animals of particular interest as recipients of bioactive compounds in the present invention are mammals, birds, fish.

A "bird" is a warm-blooded vertebrate of the class Aves. "Cellular immunity" can be achieved through cytotoxic T lymphocytes or through delayed-type hypersensitivity that involves macrophages and T lymphocytes, as well as other mechanisms involving T cells without a requirement for antibodies.

A "chimeric protein" is created when two genes that normally code for two separate proteins are combined, either naturally or as the result of human intervention, to make a protein that is a combination of all or part of each of those two proteins.

"Cxc" is *Clavibacter xyli* subspecies *cynodontis*, a bacterium.

An "endophytic microorganism" is a species of bacterium or fungus that can live within a plant and colonize the tissue and organs of that plant. It is not sufficient that the microorganism can live on the exterior of the plant.

A "fish" is a cold-blooded aquatic vertebrate, having gills and fins.

"Genetically transforming a microorganism" means adding one or more genes that the microorganism does not naturally have.

"Humoral immunity" is the result of IgG antibodies and IgM antibodies in an animal's serum.

An "immunologic compound" is one that induces either protective immunity or systemic tolerance.

A "plant" for purposes of this patent application include liverworts (Hepaticae), mosses (Musci), psilopsids (Psilopsida), club mosses (Lycopsida), horsetails (Sphenopsida), ferns and seed plants, and certain fungi specified below. Ferns and seed plants together make up the Pteropsida. Seed plants include gymnosperms (Gymnospermae) and angiosperms (Angiospermae). The great majority of plants used for food are angiosperms. For purposes of this patent application, fungi, bacteria, algae, and single-cell eukaryotes, are not considered to be plants.

The term "plant tissue" includes any tissue of a plant. Included are whole plants, any part of plants, plant cells, plants seed, and plant protoplasts. "Protective immunity" is the ability of an animal, such as a mammal, bird, or fish, to resist, as the result of its exposure to an antigen of a pathogen, a disease and/or death that otherwise follows contact with the pathogen itself. Protective immunity is achieved by one or more of the following mechanisms: mucosal, humoral, or cellular immunity. Mucosal immunity is primarily the result of secretory IgA (sIgA) antibodies on mucosal surfaces of the respiratory, gastrointestinal, and genitourinary tracts. The sIgA antibodies are generated after a series of events mediated by antigen-processing cells, B and T lymphocytes, that result in sIgA production by mucosal epithelial cells at the mucosal surfaces of the body. Mucosal immunity can be stimulated by an oral vaccine.

A "protein of a pathogen" is a protein that is coded for by the genetic material of that pathogen.

"Systemic tolerance" results when an animal ceases to respond immunologically (e.g, by exhibiting cellular, humoral, or mucosal immunity) to an antigen because of repeated previous exposure to that antigen.

Aspects of the Invention

In one general aspect, the invention is a synthesis/delivery process for synthesizing and delivering a bioactive compound to an animal, said compound being bioactive by virtue of the fact that it can induce a therapeutic, biochemical or immunological response in said animal, said method comprising the steps of:

1) ("a transformation step") genetically transforming (by gene transfer or mutation) a microorganism so that it acquires the ability to synthesize a bioactive compound while replicating itself in a plant, said microorganism being a bacterium or a fungus, 2) ("a culture/synthesis step") culturing the genetically transformed microorganism so that it synthesizes said bioactive compound; and 3) ("an administration/delivery step") administering said bioactive compound synthesized during step (2) to an animal so that said bioactive compound induces a therapeutic, biochemical, or immunological response in said animal, and wherein step (2) either takes place in a plant or does not take place in a plant.

In one embodiment of the synthesis/delivery process, in the administration/delivery step, the bioactive compound is free of plant material and the genetically transformed microorganism.

In another embodiment of the synthesis/delivery process, in the administration/delivery step, the bioactive compound is in the genetically transformed microorganism but free of plant material.

In another embodiment of the synthesis/delivery process, in the administration/delivery step, the culture/synthesis step is accomplished by infection of a plant with said genetically transformed microorganism and in the administration/delivery step, the bioactive compound either is in the plant material derived from the plant used in the culture/synthesis step or is in the genetically transformed microorganism in said plant material.

In one aspect of the synthesis/delivery process, the microorganism genetically transformed in the transformation step is a microorganism that was obtained from a plant prior to the transformation step or, alternatively, is a descendent of a microorganism that was obtained from a plant prior to the transformation step.

In an embodiment of the synthesis/delivery process of particular interest, as a result of the administration/delivery step, the bioactive compound induces an immunological response in the animal.

In particular embodiments of the synthesis/delivery process, the animal to which the bioactive compound is administered is a mammal.

Bacteria (especially gram positive bacteria, more especially gram positive bacteria of the genus Clavibacter, most especially the species *xyli* and most particularly the subspecies *cynodontis*) are microorganisms of particular interest for use in the synthesis/delivery process. The ATCC number for *Clavibacter xyli* subspecies *cynodantis* is 33973. Note that during multiplication in its host plant over the growing season that Cxc will lose by reversion the bioactive gene it was engineered by gene transfer to contain.

If the culture/synthesis step is accomplished by infection of a plant, then preferably the microorganism does not cause disease in the plant.

Whether or not a microorganism is capable of replicating itself in a plant can be determined by infecting the plant with a known number of such microorganisms and determining whether the number of such microorganisms increases with time. Methods for making such determinations are well known.

In many cases, especially when the bioactive compound is a large protein without structural features that favor its excretion by the microorganism, the bioactive compound will remain inside the microorganism (i.e, totally inside the microorganism or part of its surface) unless the plant material is disrupted prior, during, or after step (3). When the bioactive compound is inside the microorganism and the microorganism is "inside the plant", then the bioactive compound is also considered to be "inside the plant", "in the plant" and "part of the plant"; should plant material with the microorganism in it be taken from the plant, then the bioactive compound is considered to be "in the plant material" and "part of plant material from that plant".

In some cases, at least some of the bioactive compound may diffuse or be actively transported out of the microorganism into the plant tissue.

In one particular embodiment of the invention, the bioactive compound is a peptide, polypeptide, or protein. In another embodiment, the bioactive compound is not a protein, but the genetic transformation of the microorganism in step (1) involves transforming the microorganism so that it synthesizes an enzyme, two or more different kinds of enzymes, or other proteins that allows the microorganism or plant to synthesize the bioactive compound.

A therapeutic response to a bioactive compound is one that slows the growth or destroys a bacterium, fungus, virus or protozoa pathogenic for the animal to which the bioactive compound is administered, or (2) results in the cure of a disease, or an alleviation of its symptoms.

A biochemical response in a human or animal is a response that achieves a change in the amount or rate of synthesis of a compound or compounds synthesized by a cell in the human or animal. Biochemical responses that affect either the amount or the rate of synthesis of the following compounds are of particular interest:

1) Proteins, especially enzymes, hormones, and antibodies;

2) Nucleic acids, especially the DNA for one or more genes, and the heterogenous nuclear RNA and/or mRNA, for a particular gene.

An immunological response is one that induces either protective immunity (mucosal, humoral, or cellular) or systemic tolerance. Generally, a biochemical response is required for an immunological response.

The route of administration in the administration/delivery step can be either parenteral or through any mucosal surface, including the oral pharynx, nasal cavity and digestive tract.

It is optional as to whether after the culture/synthesis step, but prior to the administration/delivery step, there are one or more purification steps that together purify the bioactive compound free or substantially free of plant and genetically transformed microorganism material. In cases, where there is no such purification step or steps, the bioactive compound synthesized in the culture/synthesis step is normally administered in the administration/delivery step by feeding (i.e., oral route of administration) the animal. When the administration/delivery step is accomplished by feeding, it is highly preferable that the edible plant be raw; i.e., has not been cooked (heated above the temperatures associated with growth, storage, and transport). Animals typically may consume the plant, an organ of the plant, pieces of the plant, a puree from the plant, or plant juice.

A prophylactic compound is one that acts to prevent a disease, generally as a result of inducing a biochemical or immunological response.

Animals vary as regards which food is edible. Plants of greatest interest include all horticultural crops which can be consumed without extensive processing or heating, including tomatoes, cucumbers, squash, peppers, egg plant, peas, beans, alfalfa, citrus fruits (e.g., oranges, lemons, grapefruit), grapes, carrots, strawberries, blueberries and other berries, bananas, dates, broccoli, cabbage, Brussel sprouts, cauliflower, turnips, cucurbits, papaya, guava, apples, cherries, apricots, pears, sunflowers.

In one important immunologic aspect of the invention, the endophytic microorganism is transformed with a gene for an antigenic protein, or antigenic portion thereof, that is otherwise normally part of the pathogen against which protective immunity is sought. The endophytic microorganism, after its introduction into the plant, synthesizes the immunogenic protein as it colonizes in the plant and, subsequently, the plant or portion thereof is administered to a mammal, bird, or fish, so as to induce protective immunity against the pathogen.

In the pathogen, especially when the pathogen is a virus, the antigenic protein or antigenic portion thereof may be part of a protein, that undergoes post-translation modification.

In the genetically transformed endophytic microorganism, the gene for the antigenic protein or portion thereof may be combined with another gene so as to create a chimeric protein.

In a related immunologic aspect of the invention, the bioactive compound is an antigenic protein that, in the absence of medical treatment, induces a detrimental autoimmunologic response on its host, and repeated administration of the antigenic protein which is produced by and presented in or on an endophytic microorganism is a means of attenuating that response until systemic tolerance, a state of immunologic nonresponsiveness is achieved. The induction of systemic tolerance is useful in the treatment of autoimmune diseases such as multiple sclerosis, rheumatoid arthritis or uveitis.

When the bioactive compound is delivered for immunologic purposes, it may be preferable to deliver it with an adjuvant or other compound in order to facilitate or improve its activity.

Diseases of particular importance for treatment by the present invention are: viral infections, bacterial infections, fungal infections, protozoan infections, diabetes, immune disorders, cancer, and heart disease.

In a preferred embodiment, genetic transformation of the microorganism in the synthesis/delivery process results in the gene or genes coding for the protein or proteins of interest being under the control of a promoter or promoters so as to maximize the amount of bioactive compound synthesized by the endophytic microorganism.

Purification of the Bioactive Compound from the Endophytic Microorganism and Plant Material When the bioactive compound is a protein and is produced in an endophytic microorganism in a plant, the steps for purifying the bioactive compound would be ones commonly used for the fractionation of a plant into its protein components and the separation of individual proteins from other components of the plant cell. Such steps would strive for protection of the native conformation of the compound of interest protein by means such as flash freezing the plant material with dry ice or liquid nitrogen. Subsequent steps could include mechanical homogenization of the frozen tissue and solubilization in a cold aqueous solvent containing a non-ionic detergent and compounds which inhibit proteolytic degradation of the proteins. Particulate material may be removed by sedimentation, centrifugation and filtration. The solubilized protein of interest may be concentrated by precipitation with ethanol or another appropriate organic solvent, and further purified by either preparative high performance liquid chromatography or immunoaffinity chromatography.

When the bioactive compound is not a protein, but rather an organic compound of small or moderate molecular weight (less than several thousand daltons), and is produced in an endophytic microorganism in a plant, methods well known in the art for the purification of pharmaceutical compounds of such molecular weight from plants can be used.

When the culture/synthesis step does not involve a plant, and it is desired to purify the bioactive compound free of other material from the endophytic microorganism, there are numerous methods well known in the art that can be used to purify the bioactive compound.

Pathogens

A pathogen is any organism—such as a virus, bacterium, fungus, or parasite, or a protein which is capable of self-replication (such as a prion)—that is capable of inducing disease in an animal. Of particular interest are pathogens that use the mucosal route of entry.

Viral pathogens against which the present inventions can be applied include, but are not limited to, the parvoviridae, papovaviridae, adenoviridae, herpesviridae, poxviridae, iridoviridae, picornaviridae, caliciviridae, togaviridae, caliciviridae, flaviviridae, coronaviridae, ortho- and paramyxoviridae, rhabdoviridae, bunyaviridae, reoviridae, birnaviridae, and retroviruses.

Fungal pathogens against which the present inventions can be applied include, but are not limited to species of Aspergillus and Candida.

Bacterial pathogens against which the present inventions can be applied include, but are not limited to, Streptococci, Staphylococci, Escherichia, Shigella, Salmonella, Vibrio, Yersinia, and Mycobacterium.

Parasitic pathogens against which the present inventions can be applied include, but are not limited to, Mycoplasma, Rickettsia, Spirochetes, protozoa, Helminthes, and roundworms (ascaris).

A parasitic organism may also be a bacterium or fungus.

The primary result of protective immunity is the destruction of the pathogen or inhibition of its ability to replicate itself and establish itself within its animal host.

Pathogens that can use the mucosal route of infection and against which the present process are expected to be particularly useful are rabies, respiratory syncytial virus, cholera, typhoid fever, herpes simplex types I and II, tuberculosis, pathogenic pneumococci, human immunodeficiency virus-1 (HIV-1) and human immunodeficiency virus-2 (HIV-2).

Methods for Genetically Transforming an Endophytic Microorganisms

Genetic transformation of an endophytic microorganism may be accomplished by any of a variety of methods commonly used for gene transfer. A reference describing techniques applicable to the genetic engineering of endophytic bacteria is: Sambrook, J., Fritsch, E. F., and Maniatis, T. 1989. Molecular Cloning: A Laboratory Manual. 2nd ed. Cold Spring Harbor Laboratory Press, New York.

Genetic transformation may include mutating a microorganism to make it endophytic for a plant of interest.

Delivery of Compounds to Human or Other Animal Subjects

If a plant is used in the culture/synthesis step and the administration/delivery steps, the plant containing the bioactive compound is fed to the animal on a regular basis consistent with the animal's maximum ability to eat such plants.

Bioactive compounds purified free of plant material are delivered by standard delivery methods used for bioactive compounds including but not limited to feeding, injection, and nasal spray.

It may be desirable to combine presentation of the primary antigens with an adjuvant or other biologically active molecule, also made in the plant or endophyte, that will stimulate and or enhance an immunological response.

Endophytic Microorganisms

Plant-infecting microorganisms that have endophytic characteristics in plant hosts include certain species of gram negative aerobic rods and cocci, such as *Pseudomonas solanacearum*, whose hosts include numerous solanaceous crops (e.g., tomatoes, peppers, and eggplants), *Xanthomonas campestris*, whose hosts include broccoli, cauliflower, and brussel sprouts, *Agrobacterium tumefaciens*, whose hosts include the majority of dicotyledonous plants.

Plant-infecting microorganisms that have endophytic characteristics in plant hosts include certain species of facultative anaerobic rods, such as *Erwinia stewartii*, whose hosts include corn.

Plant-infecting microorganisms that have endophytic characteristics in plant hosts include certain species of gram-negative bacteria, such as *Azospirillum lipoferum*, whose hosts include most graminacious crops (e.g., wheat), and *Acetobacter diazotrophicus*, whose hosts include sugar cane.

Plant-infecting microorganisms that have endophytic characteristics in plant hosts include certain species of gram-positive bacteria and Actinomycetes, such as *Corynebacterium michiganense*, whose hosts include most solanaceous plants (e.g., tomatoes, peppers, and eggplant), *Clavibacter xyli*, whose hosts include sugar cane, corn and sorghum, and *Streptomyces ipomoea*, whose hosts include sweet potatoes.

Plant-infecting microorganisms that have endophytic characteristics in plant hosts include certain fungal species that are traditionally classified as endophytic and are members of the genera: Acremonium, Balancia, Atkinsonella, Balansiopsis, Epichloe, Myrigenospora, and Claviceps. Fungi traditionally classified as endophytic have a very broad host range in the grasses.

Plant-infecting microorganisms that have endophytic characteristics in plant hosts include certain genera of fungi that are traditionally classified as pathogenic for plants, such as Rhizopus, Endogone, Erysiphe, Diaporthe, Giberella, Diploidia, Alternia, Aspergillus, Botrytis, Fusarium, and Verticillium. Fungal genera traditionally classified as pathogenic for plants contain numerous species and consequently have a very broad host range.

Plant-infecting microorganisms that have endophytic characteristics in plant hosts include certain fastidious and wall-less prokaryotes such as *Spiroplasma citri*, whose hosts include citrus plants, Mycoplasma Sp., whose hosts include corn, and, *Xylela fastidiosum*, whose hosts include grapes.

EXAMPLES

Example 1

Media, Assays, Vectors, Transformation, and Plant Infection, in the Examples

Media

Growth of *E. coli* was in LB:

10 g/L bacto-tryptone (Gibco)

5 g/L basto-yeast extract (Gibco)

10 g/L NaCl

For growth on plates, 15 g/L bacto-agar (Gibco) was added.

For growth of ampicillin resistant bacteria, ampicillin (Sigma) was added to a final concentration of 50 μg/ml.

Growth of Cxc was in S8:

8 g/L Soytone (Difco)

350 mg/L Potassium Phosphate, dibasic 1.1 g/L Potassium Phosphate, monobasic 200 mg/L Magnesium Sulfate, heptahydrate The medium was autoclaved in a total volume of 940 mls. For growth on plates, 17 g/L cornmeal agar (Becton Dickinson) was included.

The following reagents were filter sterilized and added in a volume of 60 mls:

500 mg cysteine 8 mls 25% glucose (w/v)

20 mls 10% BSA (bovine serum albumin)

1.5 mls 1% hemin chloride in 0.5 N NaOH

For growth of tetracycline (Sigma) resistant bacteria, tetracycline was added to a final concentration of 1 $\mu$g/ml.

For growth of chloramphenicol resistant bacteria, chloramphenicol (Sigma) was added to a final concentration of 25 $\mu$g/ml.

1× TBS-T 20 mM Tris, pH 7.4

0.9% (w/v) NaCl 0.1% (v/v) Tween

1× Tris-glycine-SDS 25 mM Tris, pH 8.6

192 mM glycine 0.1% (w/v) SDS (Sodium dodecyl sulfate)

1× Tris-glycine 25 mM Tris, pH 8.6

192 mM glycine

2× Protein Gel Loading Buffer 62.5 mM Tris, pH 6.8

10% (v/v)glycerol

5% (v/v) β-mercaptoethanol

2% (w/v) SDS (sodium dodecyl sulfate)

0.01% (w/v) Bromphenol Blue

All enzymatic reactions (restriction digests, ligations, phosphatase reactions, PCR reactions) were performed in buffers supplied by the enzyme manufacturer.

Restriction Digests

Typical restriction digests included 1 $\mu$g of plasmid DNA and 5 U of enzyme (e.g. EcoRI) in a final volume of 20 $\mu$l. Reactions involving larger amounts of DNA were scaled up appropriately. Reactions were performed at 37° C. for 1 h unless otherwise indicated.

Phosphatase Reactions

Typical phosphatase reactions included 1 $\mu$g of plasmid DNA and 10 U of calf intestinal alkaline phosphatase in a final volume of 50 $\mu$l. Reactions were incubated at 37° C. for 1 h unless otherwise indicated.

Ligase Reactions

Typical ligase reactions included roughly 1 $\mu$g of DNA and 5 U of T4 DNA ligase. Reactions were incubated overnight at 16° C.

PCR Reactions

PCR reactions included 10 ng of template DNA (either plasmid DNA or Cxc genomic DNA), 0.25 $\mu$M each primer, 1.5 mM $MgCl_2$, 200 $\mu$M each of dATP, dTTP, dCTP, and dGTP, 50 mM KCl, 10 mM Tris, pH 8.4, 2.5 U Taq polymerase and 50 $\mu$l mineral oil. The annealing temperature was determined by the sequence of the primers, but was typically 56° C. A typical PCR reaction was performed for 40 cycles with 1 min. at 94° C., 1 min at 56° C., and 2 min. at 72° C. per cycle in a MiniCycler from MJ Research.

Plasmids pRN, a plasmid that contained the rabies nucleoprotein (N) gene (the gene for rabies N protein) was obtained from Dr. Zhen Fang Fu of Thomas Jefferson University. Primers complementary to the 5' and 3' ends of the rabies N gene were synthesized at the Thomas Jefferson University Nucleic Acid Facility. The sequences are:

a) N-5': 5'-CAGCACCCATGGATGCCGACAAGATTG-3' (SEQ ID NO:1). This primer has an NcoI restriction site at the translation start, b) N-3'-1: 5'-GCGAGAAGCTTGAATTCCTTCT-TATGAGTCACTCG-3' (SEQ ID NO:2). This primer has an EcoRI site immediately adjacent to the N sequence and a HindIII site adjacent to the EcoRI site, c) N-3'-2: 5'-GCGAGCTCGAGCTTCTTATGAG-TCACTCG-3' (SEQ ID NO:3). This primer has an XhoI site immediately adjacent to the N sequence.

Figure 2:
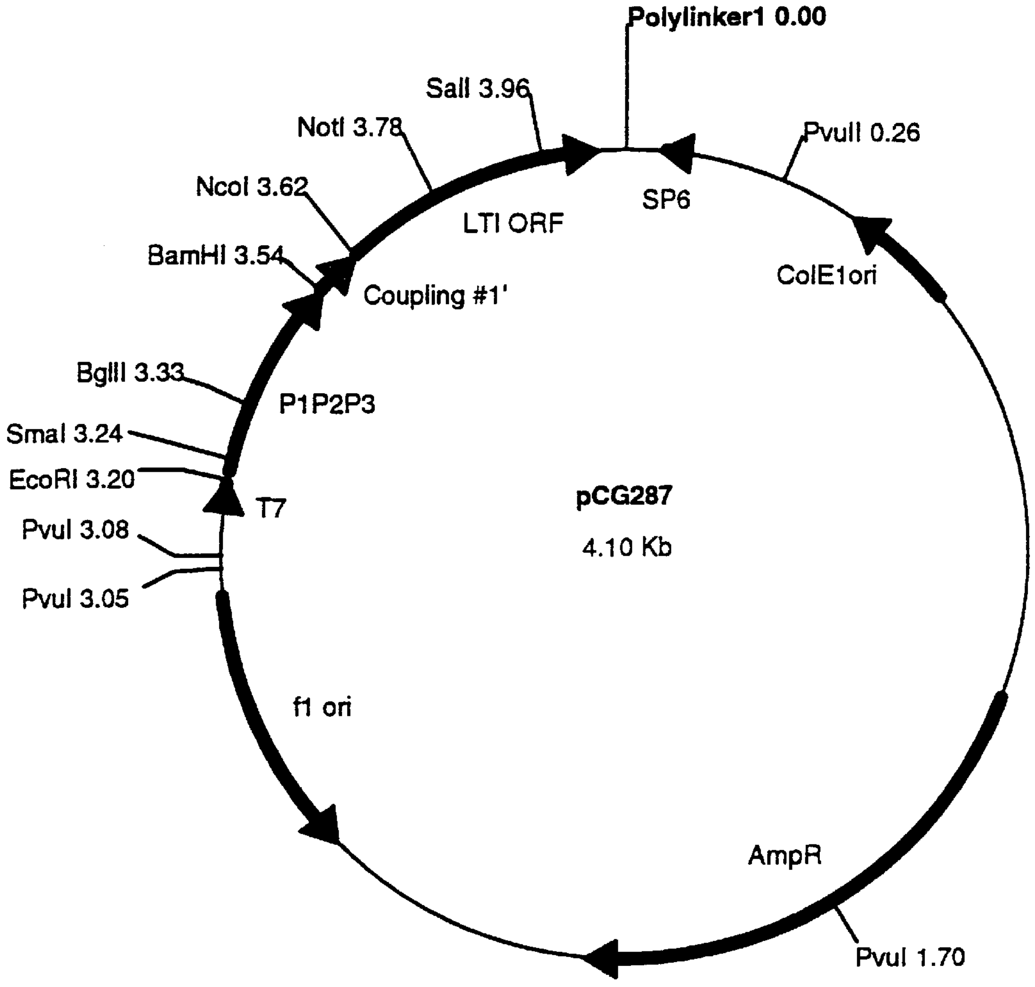
FIG. 2. Map of plasmid pCG287.
Figure 3:
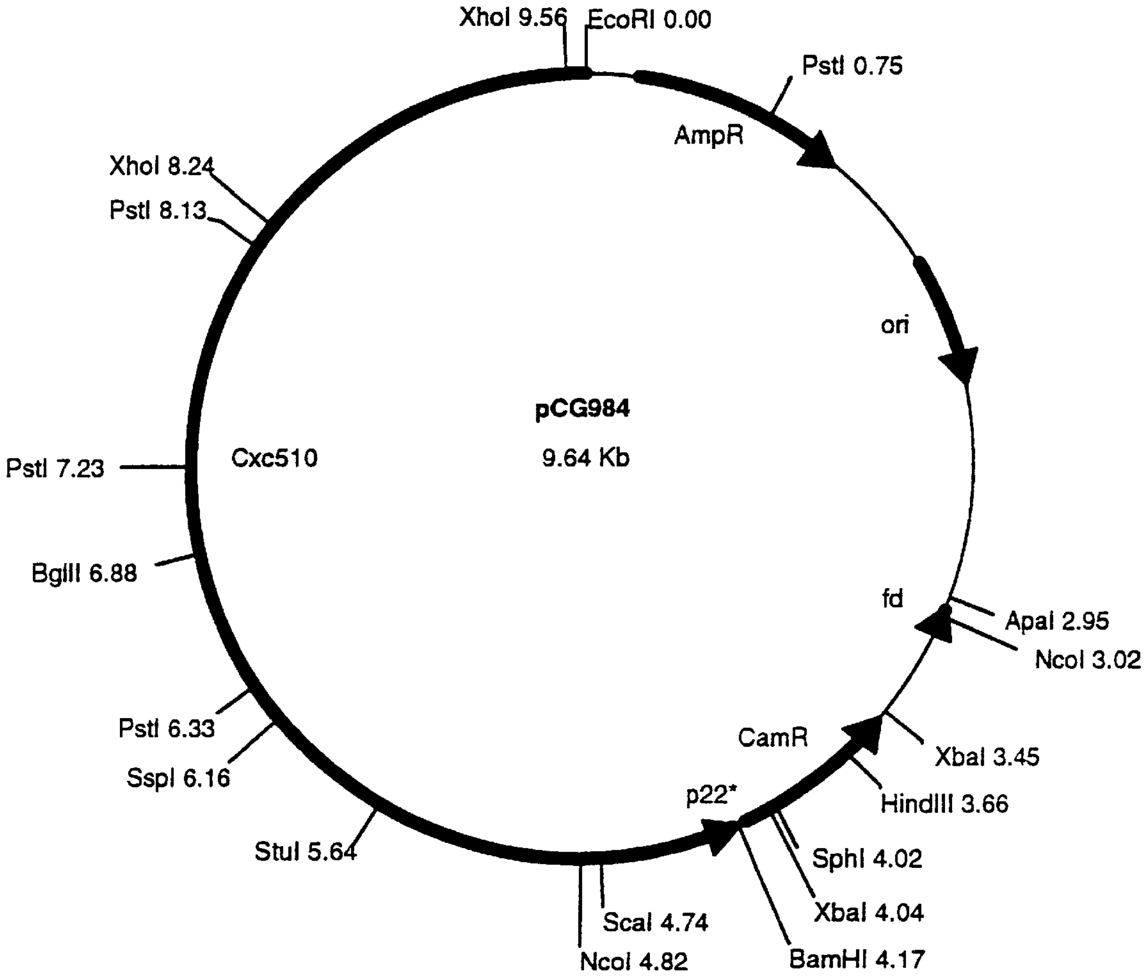
FIG. 3. Map of plasmid pCG984.
Figure 4:
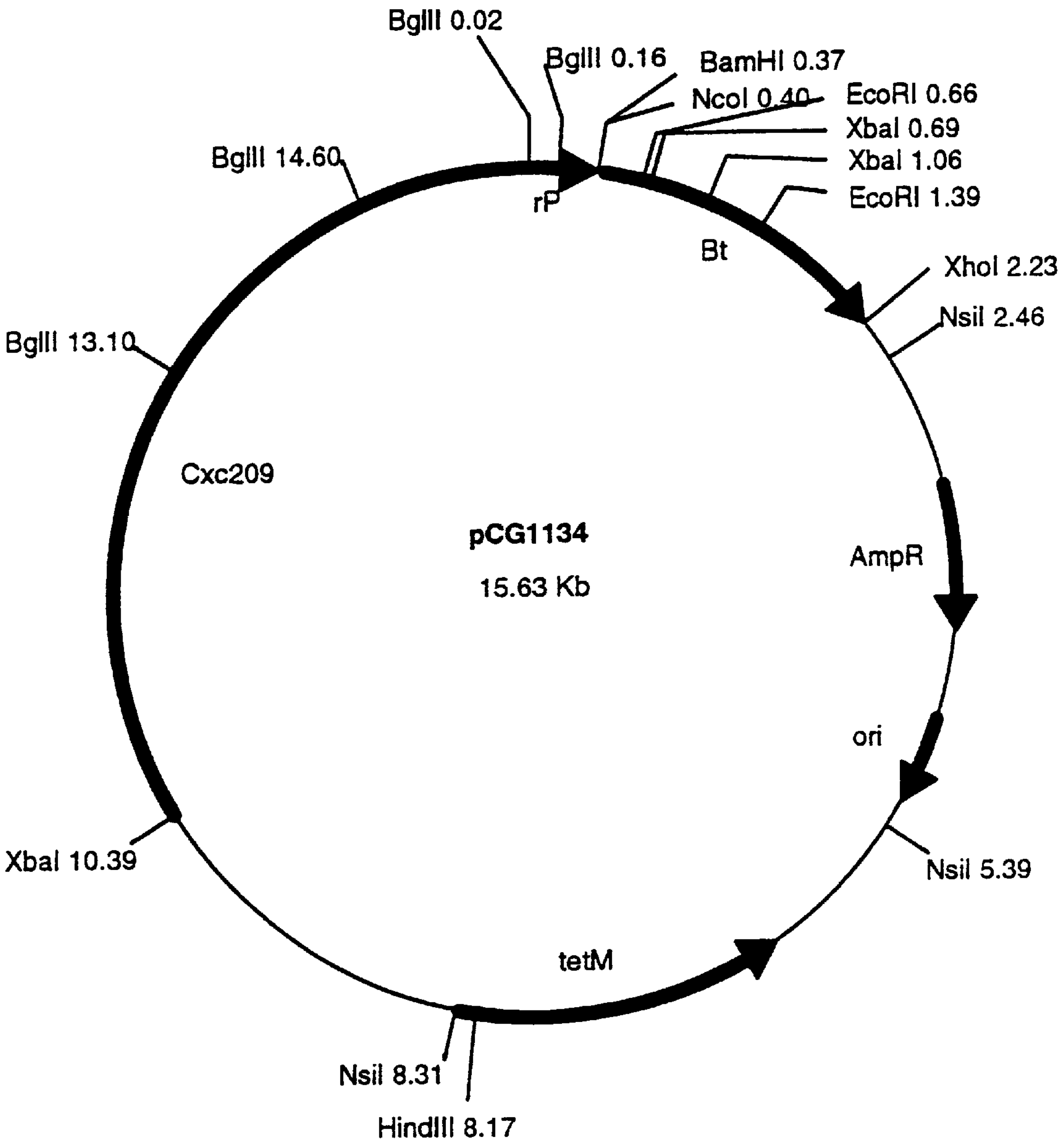
FIG. 4. Map of plasmid pCG1134.
Figure 5:
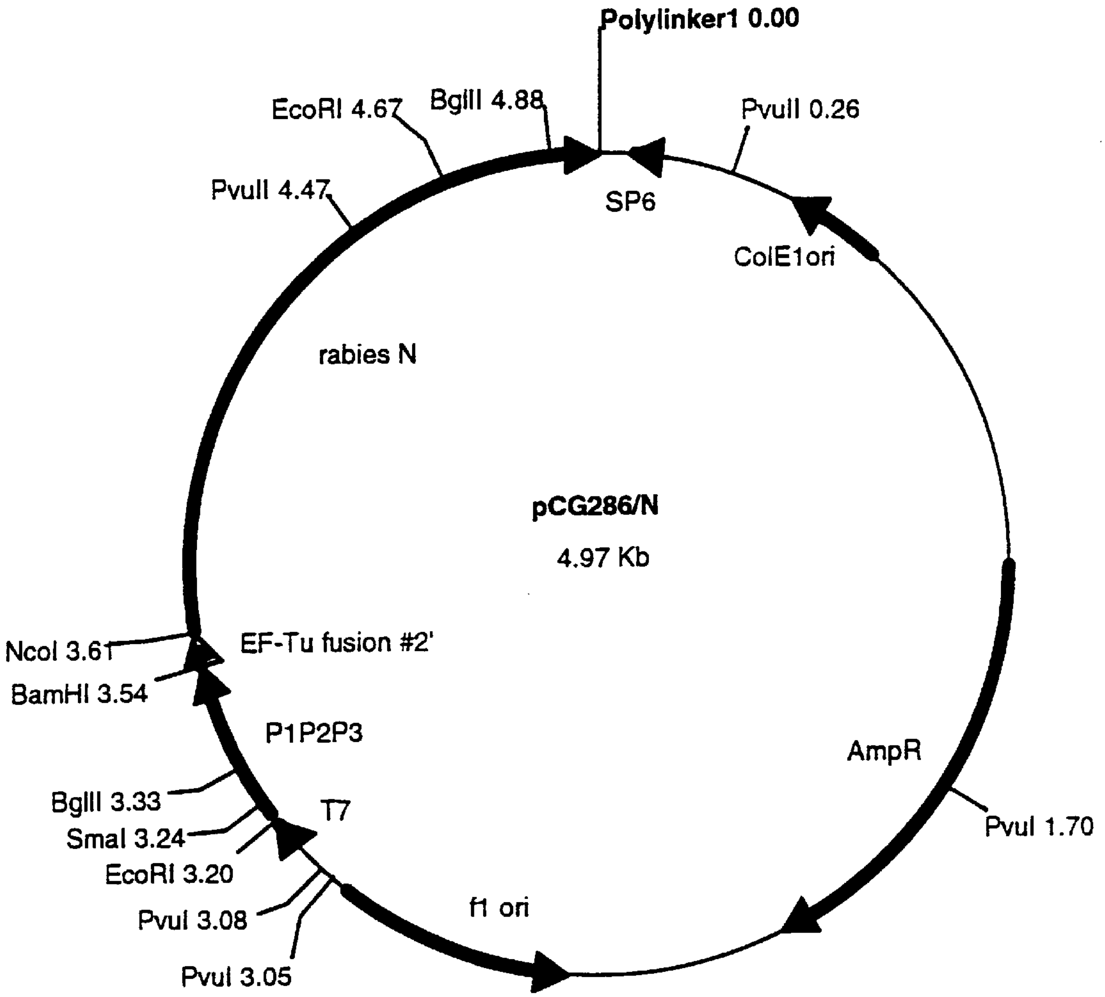
FIG. 5. Map of plasmid pCG286/N.
Figure 6:
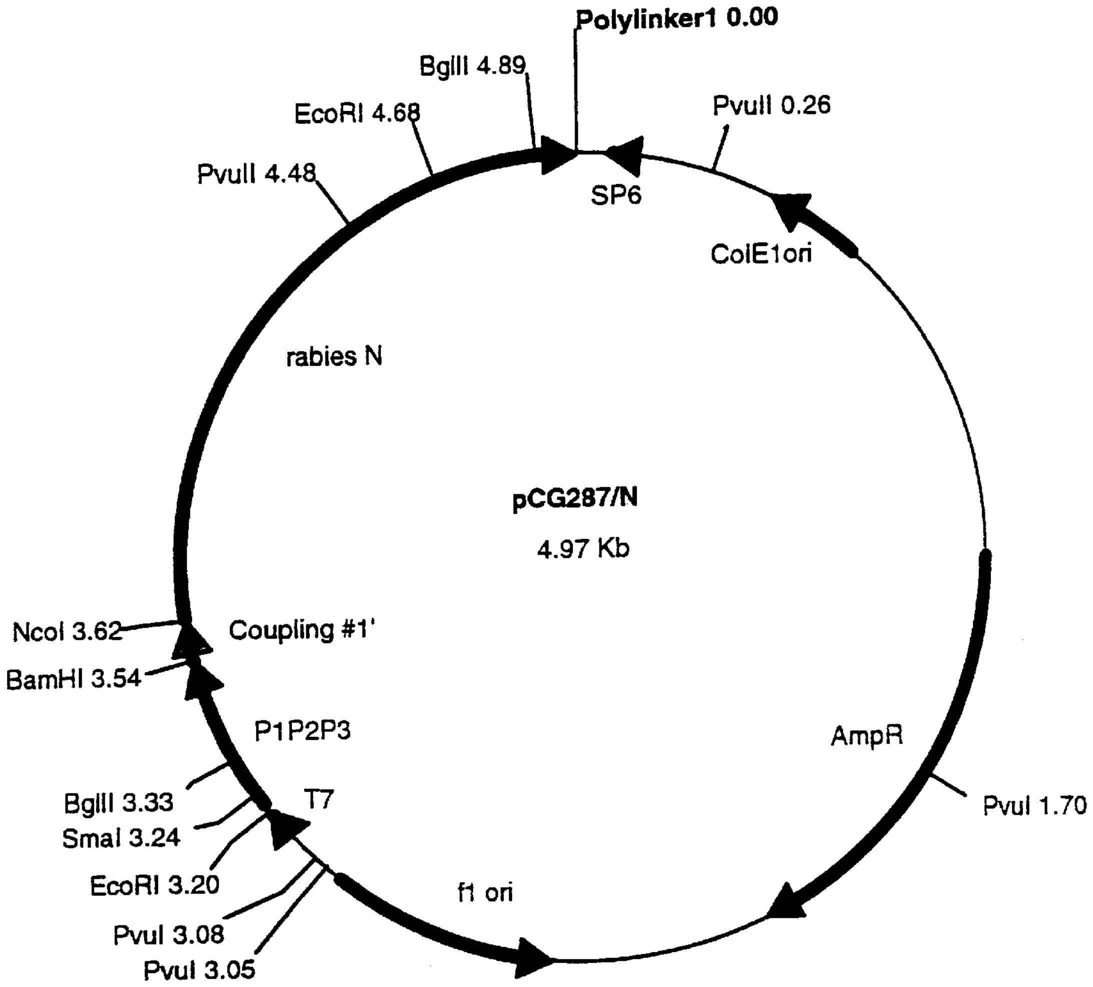
FIG. 6. Map of plasmid pCG287/N.
Figure 7:
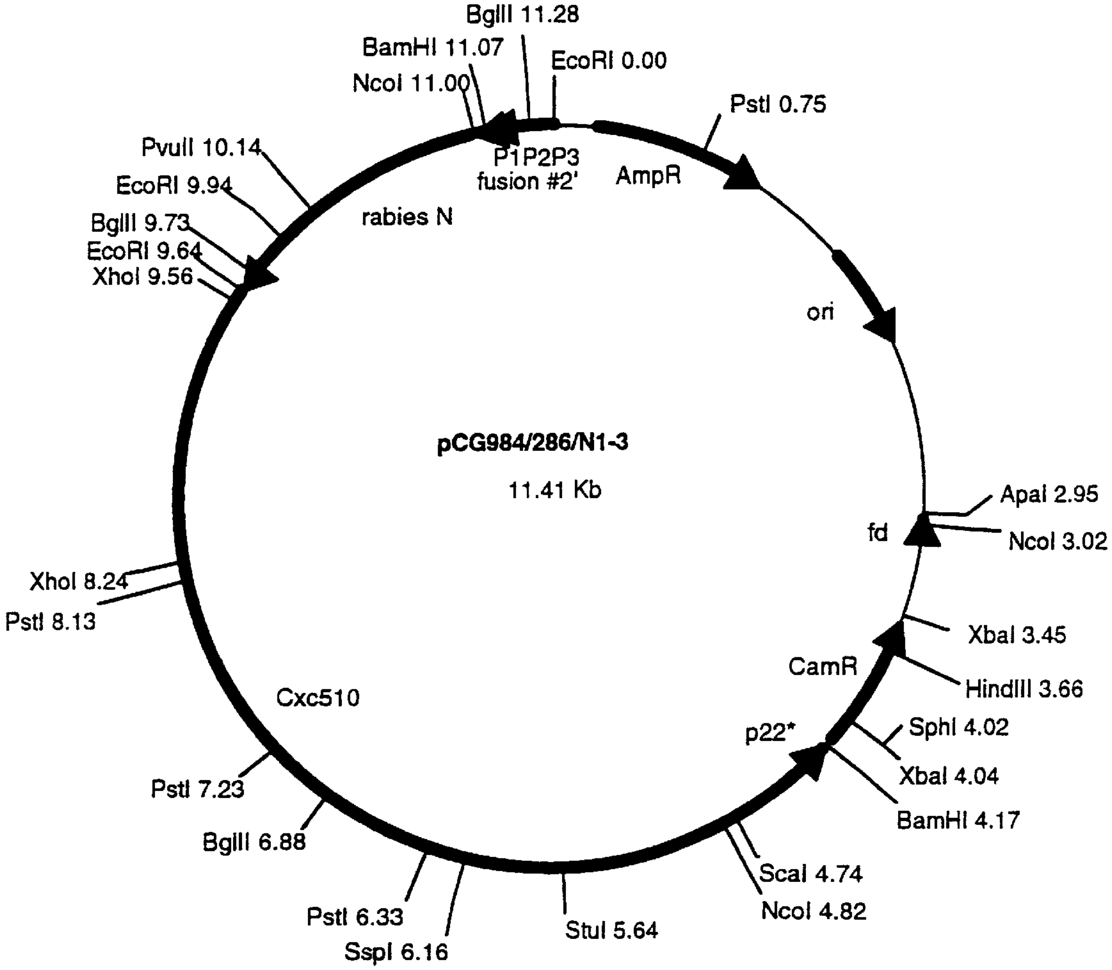
FIG. 7. Map of plasmids pCG984/286/N1-3 and pCG984/286/N1-4.

These primers were used to construct clones.

pCG286 (See FIG. 1)

pCG286 is derived from pGEM-3Zf (Promega). It contains: a) an *E. coli* origin of replication (ColEl ori), b) a β-lactamase gene that provides ampicillin resistance (amp R), c) a bacteriophage f1 origin of replication (f1 ori), d) promoters for RNA polymerases from bacteriophages T7 and SP6, e) a Cxc rRNA promoter (P1P2P3), f) a translation initiation sequence (EF-Tu fusion #2'), and g) a gene encoding a trypsin inhibitor (LTI ORF).

pCG287 (See FIG. 2)

pCG287 is identical to pCG286 with the exception of the translation initiation sequence (coupling #1').

pCG984 (See FIG. 3)

pCG984 contains: a) an *E. coli* origin of replication (ori), b) a β-lactamase gene (AmpR), c) a bacteriophage fd transcription termination sequence, d) a chloramphenicol resistance gene (CamR), e) an RNA polymerase promoter from bacteriophage p29 (p22*) and f) a 5395 bp segment of Cxc genomic DNA (Cxc510). In FIG. 3, the BamHI 4.17 site is just outside the Cxc510 segment. A stock of pCG984 is stored in the laboratory of Dr. Hilary Koprowski of Thomas Jefferson University, Philadelphia, Pa. The plasmid pCG984 has been deposited with the American Type Culture Collection (ATCC), Rockville, Md., U.S.A. and has been assigned ATCC designation 97320. Plasmids identical to or functionally equivalent to pCG984 can be constructed on by persons of ordinary skill in the art based on the information disclosed herein. Of related interest is that the portion of the Cxc segment between the XhoI 8.24 site and the XhoI 9.56 site is not considered important for the integration function of the Cxc segment. Additionally the Cxc fragment is so large that some portions at the end joined to the p22* insert are not considered important for integration. Fragments of Cxc can be prepared by digestion of Cxc DNA with appropriate restriction enzymes (e.g. XhoI and ScaI), elimination of undesired co-electrophoresing segments by treatment with restriction enzymes that do not attack the desired Cxc segment (see FIG. 3), electrophoresis to isolate Cxc segments of the desired size, followed by joining it to a construct that corresponds to the portion of pCG984 not including the Cxc segment.

pCG1134 (See FIG. 4)

pCG1134 contains: a) an *E. coli* origin of replication (ori), b) a β-lactamase gene (AmpR), c) a tetracycline resistance gene (tetM), d) a Cxc rRNA promoter (rP), e) the cryIa(c) gene of Bacillus thuringiensis which encodes a delta-endotoxin (Bt), and f) a 5241 bp segment of Cxc genomic DNA (Cxc209). That segment is distinct from the Cxc genomic segment in pCG984. The Cxc209 segment is discussed in T. S. Lampel et al., Applied and Environmental Microbiology, Vol. 60, pp. 501–508 (1994)

pCG286/N (See FIG. 5)

pCG286/N is identical to pCG286 except the gene encoding the trypsin inhibitor has been removed and replaced. pCG286 was digested to completion with NcoI and HindIII. The large (3620 bp) fragment was gel purified and treated with calf intestinal phosphatase. PCR was used to amplify the N Gene from pRN using primers N-5' and N-3'-1. The resulting DNA was digested to completion with NcoI and HindIII, ligated to the phosphatased pCG286 fragment and transformed into *E. coli*. The presence of N in ampicillin resistant colonies was confirmed by restriction analysis and by PCR with primers N-5' and N-3'-1.

pCG287/N (See FIG. 6)

pCG287/N is identical to pCG287 except the gene encoding the trypsin inhibitor has been removed and replaced with the gene for rabies N. This clone was prepared the same way as pCG286/N clone but beginning with the pCG287 vector.

pCG984/286/N1-3 and pCG984/286/N1-4 (See FIG. 7)

pCG984/286/N is identical to pCG984 except that a 1781 bp EcoRI fragment of pCG286/N that contains the Cxc rRNA promoter and rabies N has been inserted in the EcoRI site. pCG984/286/N1-3 contains the insert oriented to transcribe toward the Cxc genomic sequence, pCG984/286/N1-4 contains the insert oriented to transcribe away from the genomic sequence.

Figure 8:
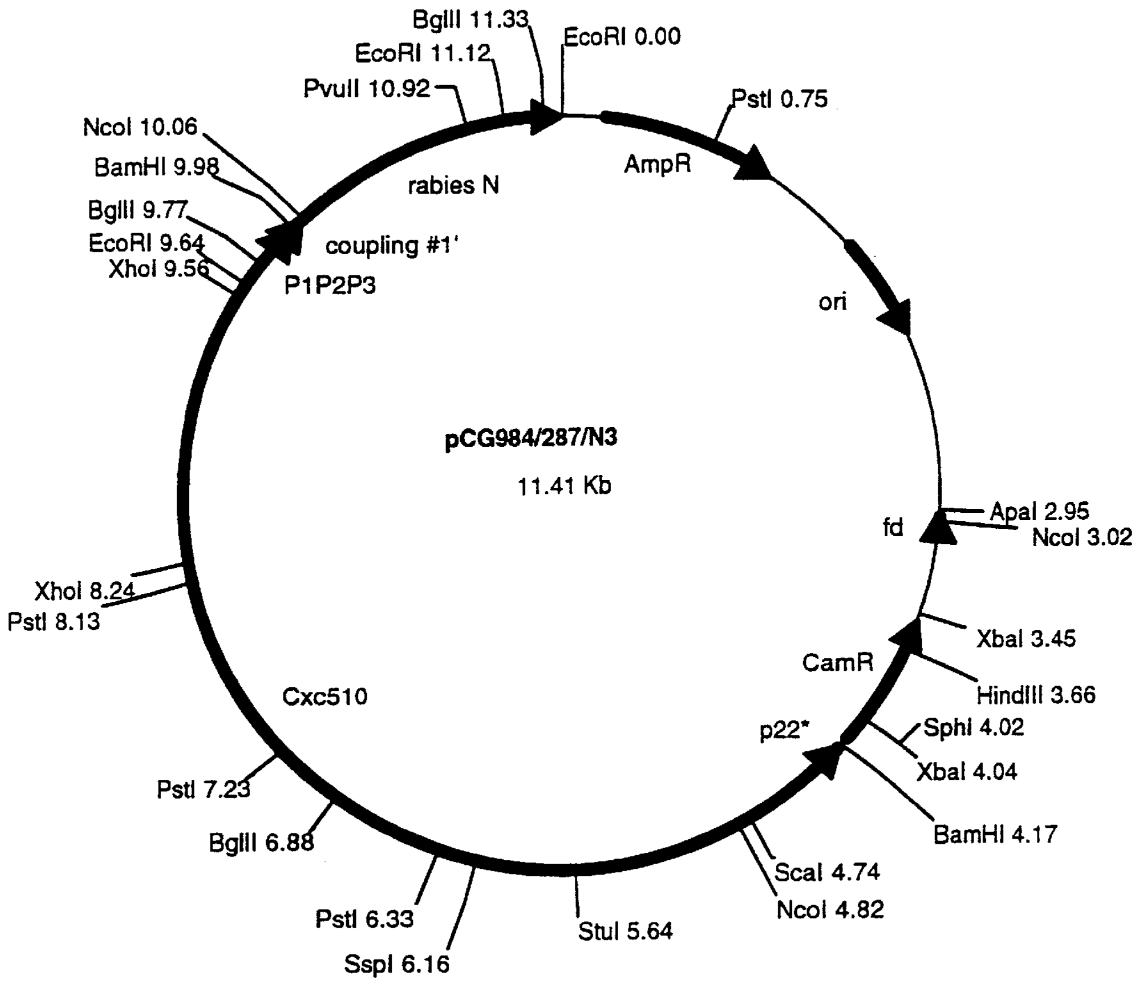
FIG. 8. Map of plasmids pCG984/287/N3 and pCG984/286/N4.

The rabies N gene contains an EcoRI site within the coding region, 309 bp away from the stop codon. Therefore, transferring the intact rabies N gene with the Cxc promoter to the plasmid pCG984 required performing an EcoRI partial digest. 5 μg of pCG286/N was digested with 3 U of EcoRI for 2 hrs at 37° C. Under these conditions, approximately half of the DNA is not cut at all, the remaining half is a mixture of plasmids cut at one, two or all three EcoRI sites. The 1781 bp EcoRI fragment containing the intact N gene, Cxc promoter and translation initiation sequence was gel purified. pCG984 was digested to completion with Eco RI, treated with phosphatase, ligated to the purified pCG286/N fragment, and transformed into *E. coli*. The presence of N in ampicillin resistant colonies was confirmed by restriction analysis and by PCR with primers N-5' and N-3'-1. Orientation of the insert relative to the Cxc genomic sequence was determined by restriction analysis.

pCG984/287/N3 and pCG984/287/N4 (See FIG. 8)

pCG984/287/N is identical to pCG984 except that a 1781 EcoRI fragment of pCG287/N that contains the Cxc rRNA promoter and rabies N has been inserted in the EcoRI site. pCG984/287/N3 contains the insert oriented to transcribe away from the Cxc genomic sequence, pCG984/287/N4 contains the insert oriented to transcribe toward the genomic sequence.

Figure 9:
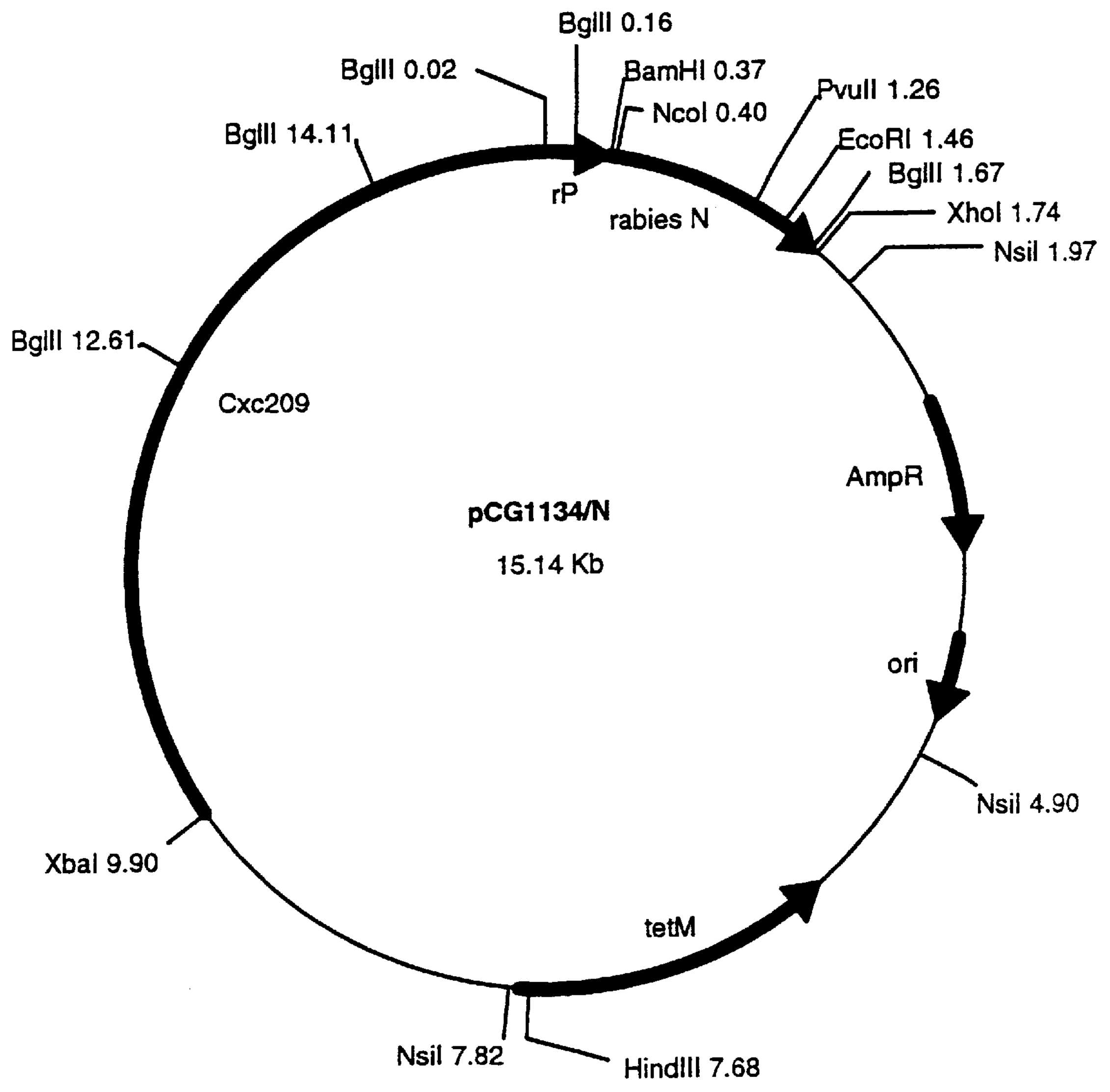
FIG. 9. Map of plasmid pCG1134/N.

This plasmid was constructed in the same way as pCG984/286/N, but beginning with 5 μg of pCG287/N.

pCG1134/N (See FIG. 9)

pCG1134/N is identical to pCG1134 except that the BT gene has been removed and replaced with rabies N.

pCG1134 was digested to completion with NcoI and XhoI. The large (13792 bp) fragment was gel purified and treated with phosphatase. PCR was used to amplify the N gene from pRN using primers N-5' and N-3'-2. The resulting DNA was digested to completion with NcoI and XhoI, ligated to the phosphatased pCG1134 and transformed into *E. coli*. The presence of N in ampicillin resistant colonies was confirmed by restriction analysis and by PCR with primer N-5' and N-3'-2.

The Sequence of Ef-Tu Fusion #2' (from pCG286) is

5'-GGATCCGCTA CACGAGAGTC CTGAGGAGGA CCCACAGTGG CTAAGGCCAA GTTCGAGCGG ACT-AAGGCCA TGG-3' (SEQ ID NO:4) where GGATCC is the BamHI site at the start of the sequence and CCATGG is the NcoI site at the end. The ATG of the NcoI site is the translational start site.

The Sequence of Coupling #1' (from pCG287) is

5'-GGATCCGCTA CACGAGAGTC CTGAGGAGGA CCCACAGTGG CTAAGGCCAA GTTCGAGCGG ACT-AAGCAGG AGGCCTGACC ATGG-3'(SEQ ID NO: 5) where GGATCC is the BamHI site at the start of the sequence and CCATGG is the NcoI site at the end. The ATG of the NcoI site is the translational start site.

The 5' end primer used to amplify the N gene (N-5', sequence: 5'-CAGCACCCAT GGATGCCGAC AAGATTG-3' (SEQ ID NO:6)) is designed so that the rabies sequence begins with the ATG start of the N gene (the first ATG from the 5' end of the primer). The rest of the primer sequence creates an NcoI site at the ATG start, that is not present in the wild type rabies N sequence, and has a six bases at the 5' end to allow efficient digestion of PCR products by NcoI. These are all removed by NcoI digestion before subcloning, so that the sequence proceeds directly from coupling #1' or EF-Tu fusion #2' to the rabies ATG start.

The 3' end primer used to amplify the N gene for cloning into pCG984 (N3'-1, sequence: 5'-GCGAGAAGCT TGAATTCCTT CTTATGAGTC ACTCG-3'SEQ ID NO:2)) was designed so that the rabies sequence ends 4 bp past the translation stop (5'-TAA GAAG-3'). This is followed by an EcoRI site (5'-GAATTC-3'), then a HindIII site (5'-AAGCTT-3'), then five extra bp to allow efficient digestion of the PCR products by HindIII.

The 3' end primer used to amplify the N gene for cloning into PCG1134 (N3'-2, sequence: 5'-GCGAGCTCGA GCT-TCTTATG AGTCACTCG-3' (SEQ ID NO:3)) was also designed so that the rabies sequence ends 4 bp past the translation stop (5'-TAA GAAG-3'). This is followed by an XhoI site (5'-CTCGAG-3') then five extra bp to allow efficient digestion of the PCR products by XhoI.

For both the pCG984 and pCG1134 derived plasmids, the rabies sequence is a total of 1357 bp. The sequence is from the Era strain of rabies. It is shown in FIG. 10, from the ATG start to the GAAG just past the TAA stop. The ATCC number for the ERA strain of rabies that contains the N gene is VR332. (see also U.S. Pat. No. 3,423,505. In pCG286 and pCG287, the sequence of the Cxc rRNA promoter from the EcoRI site at the beginning of the sequence to the BamHI site at the beginning of the translational leader is:

5'-GA ATTCTGATCA GATCCGGAGT TCCGGC-GAAG TCAACCTCGA CACGCCCGGG TTGTCAGTCG AATTTGCACG CTCTCGGGGG ACCTGCGTAA AGTACTTACT TGTCACCCCA AAGGTGCGGG AGAGAGGAAG ATCTCCCCGG CCTCAAGTGG GAC-CAAGATC CTTAGTTAGC GGCAATCTGA GCTTGT-GAAA GTTCGTTTGT ATCGCTTAGA ATAAATACCC CACTCACTGG ACAGGTCTAA TCGCTTCGGA TCGC-GAGCAG TCGGATGTAT CCCACGATGG ATGAAC-GAAA AGCGCGAAAC GGACAGCTTG ACAAACT-GAC CGAGAGTGGT AAGATAGCGA AGGATCC-3' (SEQ ID NO:7)

DNA Isolation from Cxc 5 mls of cells grown to saturation were harvested by centrifugation, resuspended in 100 μl 10 mM Tris, pH 7.6, 1 mM EDTA (TE) plus 200 μg of lysozyme (Sigma) and incubated at 37° C. for 1 hr. To this mixture was added 25

$\mu$l 0.5 M EDTA and 15 $\mu$l 10% SDS. The reaction was incubated at 37° C. for 2 h. 150 $\mu$l of phenol was added. The mixture was vortexed for 30 sec, incubated at room temperature for 10 min and vortexed again. 150 $\mu$l of chloroform was added. The mixture was vortexed for 30 sec and centrifuged at 14000 rpm for 10 min. The aqueous phase was removed and placed on ice. 200 $\mu$l TE was added to the organic phase. The mixture was vortexed for 30 sec and centrifuged at 14000 rpm for 10 min. The aqueous phase was removed and pooled with the previous aqueous phase. The organic phase was discarded. 200 $\mu$l of phenol/chloroform/isoamyl alcohol (25:24:1 v/v/v) was added to the aqueous phase. The mixture was vortexed for 30 sec and centrifuged at 14000 rpm for 10 min. The organic phase discarded. 1 $\mu$l of a 1 $\mu$g/$\mu$l solution of RNAse A was added, along with 15 $\mu$l of 5 M NaCl and 600 $\mu$l absolute ethanol. The sample was centrifuged at 14000 rpm for 15 min. The supernatant was discarded, the pellet was rinsed once with 70% ethanol and redissolved in 20 $\mu$l water.

Western Blots

To prepare protein from Cxc, 25 mls of bacteria were grown to saturation in S8 media (with antibiotics if necessary) and then spun at 4000 rpm for 15 min. to pellet the cells. The cell pellet was washed once with water and resuspended in 1 ml water. 150 $\mu$l of concentrated cells were added to 150 $\mu$l of 2× protein gel loading buffer, vortexed for 20 sec, boiled for 5 min. and placed on ice. The mixture was passed 5 times through a 23 gauge needle to shear DNA released from the lysed cells, then spun at 1400 rpm in a microfuge for 10 min. 10 $\mu$l of the supernatant was loaded in a well of a 10% acrylamide protein gel. The gel was run at 200 V for 45 min. in 1× Tris-glycine-SDS. Purified BT protein to be used as a standard was obtained from Crop Genetics and from Ecogen. Purified rabies N protein to be used as a standard was obtained from Dr. Zhen Fang Fu of Thomas Jefferson University.

After electrophoresis, the gel was soaked in cold 1× Tris-glycine for 15 min. The separated proteins were transferred onto a polyvinylidene difluoride (PVDF) membrane (DuPont NEN) by electrophoresis at 150 V for 1.5 h in 1× Tris-glycine.

Proteins were detected with a Vectastain kit (Novocastra Laboratories). Briefly, after transfer, the membrane was soaked overnight in 5% milk to block any non-specific binding. The membrane was washed 3 times in 1× TBS-T, incubated for 1 h at 37° C. in 5 mls TBS-T plus 1–10 $\mu$l rabbit polyclonal antiserum (anti-N antiserum was obtained from Dr. Fu, anti-BT antiserum was obtained from Crop Genetics), washed 3 times in TBS-T, incubated for 30 min at 37° C. in 10 mls TBS-T plus 1 drop anti-rabbit antiserum (from Vectastain kit), washed 3 times in TBS-T, incubated for 30 min at 37° C. in 5 mls TBS-T plus 2 drops each solutions A and B (from Vectastain kit), washed 3 times in TBS-T, incubated in 5 mls diaminobenzidine peroxidase substrate in urea hydrogen peroxide (Sigma Fast tablet set, Sigma) until developed, washed in water and dried.

Cxc Transformation

Wild type Cxc was grown in S8 medium without antibiotics to an $OD_{600}$ of 0.2. Cells were collected by centrifugation at 4000 rpm in a Beckman GS-6R tabletop centrifuge. Cells were washed twice with cold water and once with cold 10% sucrose. The final cell pellet was resuspended in 200 $\mu$l of cold 10% sucrose per initial 25 mls of culture and kept on ice to be used that day. 50 $\mu$l of these cells were placed in a pre-chilled 2 mm electroporation cuvette with 1 $\mu$l (approx. 1 $\mu$g) of pCG984/N1-3 or pCG984/N1-4, incubated on ice for 5 min. and pulsed at 129 ohms, 2.5 kV in a BTX Electro Cell Manipulator 600. After the pulse, cells were put back on ice for 5 min. 400 $\mu$l of S8 without antibiotics was added and cells were incubated at 30° C. overnight. The next day, the entire 450 $\mu$l was plated onto a single plate of S8 plus 25 $\mu$g/ml chloramphenicol and incubated at 30° C. for two weeks. Chloramphenicol resistant colonies were inoculated into liquid S8 plus 25 $\mu$g/ml chloramphenicol and the presence of the rabies N gene confirmed with PCR. Expression of N was confirmed by Western blot.

Preparation of Cxc Containing the BT Gene for Administration to Mice in Example 2

Cxc containing the BT gene (strain MDR1.1413) was grown in liquid S8 medium containing 1 $\mu$g/ml tetracycline at 30° C. for approximately one week, at which time growth had ceased. Cells were harvested by centrifugation, washed twice with water, once with 10% sucrose and resuspended in 10% sucrose to a final $OD_{600}$ of 12 (=$1\times10^{10}$ cfu/100 $\mu$l) to be used for testing in mice. Final cell density was confirmed by plating serial dilutions of an aliquot on S8 plus tetracycline. Expression of BT was confirmed by Western blot.

Preparation of Cxc Expressing the Rabies N Gene for Administration to Mice in Example 3

Cxc expressing N is prepared as described in Example 2, except that the S8 medium contains 25 $\mu$g/ml chloramphenicol instead of tetracycline.

Culturing of Corn Kernels Infected with Cxc Expressing the Rabies N Gene in Example 4

Corn kernels are infected as described in below (seed infusion) with Cxc expressing rabies N. Kernels are germinated in soil for approximately 2 weeks, at which time approximately 4 leaves are visible. Shoots are cut away from roots, washed to remove soil and fed to mice. To determine the extent of colonization of the corn with Cxc, pieces of each leaf are weighed, surface sterilized with ethanol and ground in a mortar and pestle. The homogenate is suspended in 10 mls of sterile water and aliquots are plated on S8 plates plus chloramphenicol. Chloramphenicol resistant colonies are counted after 2 weeks at 30° C. and the presence of N in representative colonies is confirmed by PCR.

Infection of Plants with Cxc

Introduction of Cxc into plants is easily accomplished by several methods including delivery into the seedling or infusion into the seed. Both methods have been refined for use with corn (Zea mays) but can be readily adapted for use with other plant species.

a. Seedling inoculation. Cxc can be introduced into emerged seedlings (approximately one to eight weeks post-emergence) by wound inoculation. This process entails the introduction of Cxc via a simple device which can deliver the bacteria into the interior of the plant. The pointed end of a sewing needle is inserted into a wooden dowel which acts as a handle. The eye end of the sewing needle is sharpened to a point while leaving the eye intact. The eye end of the needle is dipped into a suspension of viable Cxc cells and then removed. The eye of the needle is now filled with a small amount of the bacterial suspension. The sharpened eye end containing the bacteria is then inserted into and through the stem or leaf bundle of the plant and then withdrawn. The Cxc delivered into the plant by this manipulation is sufficient to establish colonization.

b. Seed infusion. A container of dry, viable seed is washed, surface sterilized, and thoroughly rinsed. The seed are soaked in aerated water for a period of 15 to 18 hours followed by a rinse with clean water. The soaked seeds are immersed in a concentrated suspension of Cxc, placed in a pressure vessel and subjected to approximately 100 pounds per square inch of pressure for approximately one hour. The pressure is then released, the seeds are removed from the vessel and rinsed. The seeds can be planted directly or they can be dried back to 13% moisture for later planting.

Example 2

Immunization and Testing Protocol for BT-transformed Cxc Free of Plant Material

The following experiment is representative of those used to confirm that transgenic Cxc expressing a foreign protein, in this case BT-toxin ("BT"), can be used to both express and deliver antigen in an immunogenic form. In this example, 8 groups of 8 week old female outbred Swiss-Webster mice were immunized per os with Cxc (wild type) or Cxc-BT [100 μl, in 10% sucrose via gastric intubation], 4 times at approximately two week intervals as detailed in Table 2 below. One group was fed 10% sucrose alone while another group received an intra-peritoneal dose of Cxc-BT [100 μl; $5\times10^9$ bacteria, 1:1 in Complete Freund's adjuvant] on day 0 and a booster dose of Cxc-BT in sucrose [100 μl containing $5\times10^9$ bacteria] 6 weeks later.

TABLE 2

| Group | Antigen | Route of administration | Dose |
|---|---|---|---|
| A | sucrose alone | p.o. | — |
| B | Cxc | p.o. | $5 \times 10^3$ |
| C | Cxc | p.o. | $5 \times 10^5$ |
| D | Cxc | p.o. | $5 \times 10^7$ |
| E | Cxc | p.o. | $5 \times 10^9$ |
| F | Cxc-BT | p.o. | $5 \times 10^3$ |
| G | Cxc-BT | p.o. | $5 \times 10^5$ |
| H | Cxc-BT | p.o. | $5 \times 10^7$ |
| I | Cxc-BT | p.o. | $5 \times 10^9$ |
| J | Cxc-BT | i.p. | $5 \times 10^9$ |

In Table 2, the Dose is in number of CFU (colony-forming units).

Two weeks after the final immunization the mice were bled, euthanized, spleens removed, and small intestinal contents flushed with 3 mls of protease inhibitor solution [0.1 mg/ml soybean trypsin inhibitor in 50 mM EDTA]. The intestinal contents were diluted in 3 mls of PBS and dispersed with Pasteur pipette, vortexed, and then centrifuged for 10 min. at 2,400 rpm. Three mls of the supernatant were transferred to a round-bottom polycarbonate centrifuge tube and 30 μl of freshly prepared 100 MM PMSF (phenymethylsulfonyl fluoride) in 95% ETOH was added. This material was aliquoted into 1.5 ml fractions and centrifuged for 30 min at 4° C. at 13,000 rpm. One ml of clarified, diluted secretory material was removed from the tubes and 10 μl of 100 mM PMSF in 95% ETOH was added. Fifteen minutes later, 50 μl of fetal bovine serum was added and the material was then frozen at −20° C. until assayed.

Figure 11:
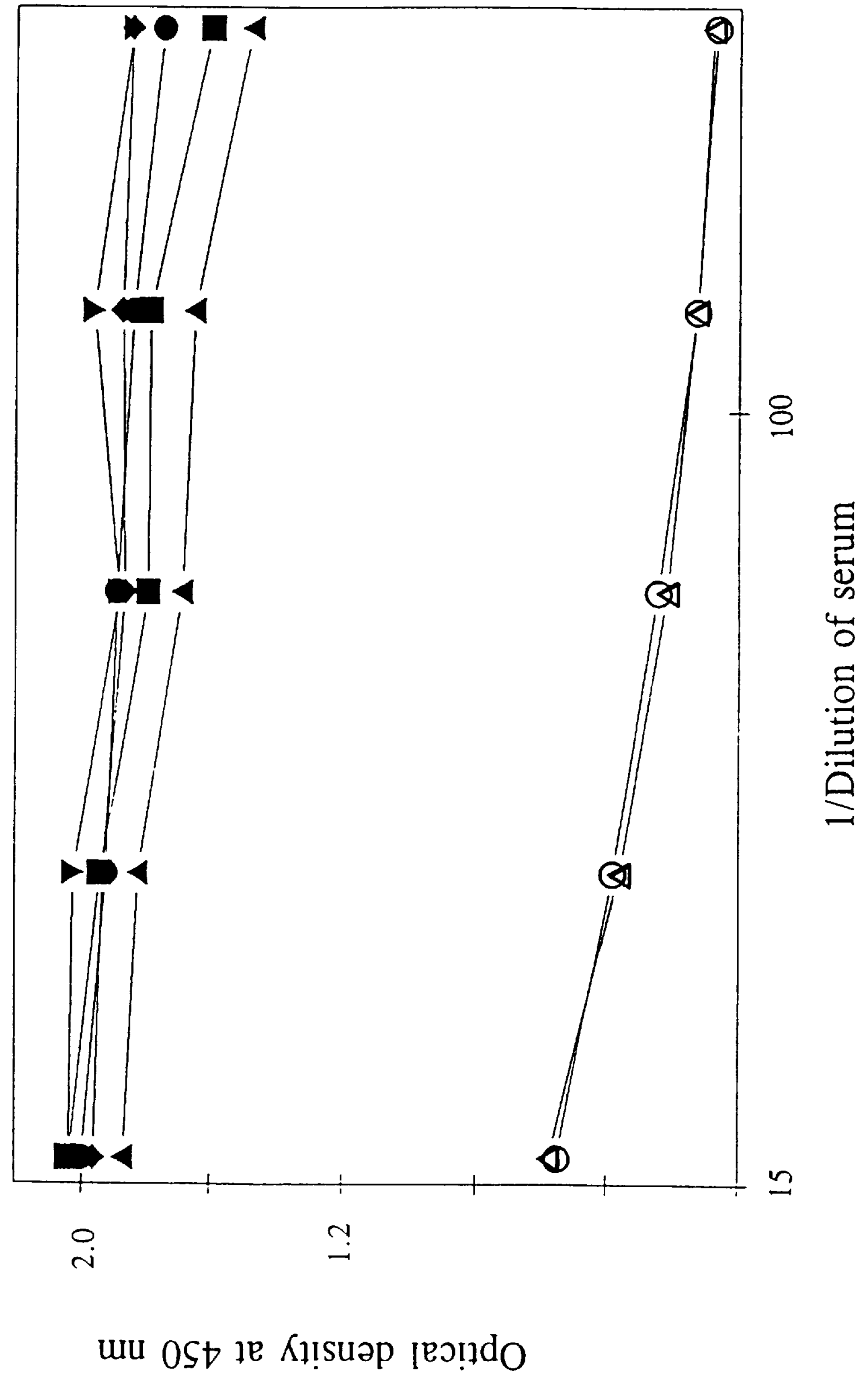
FIG. 11. Serum BT-specific antibody response of mice immunized intraperitoneally with Cxc-BT. Open symbols are for results obtained with the controls (10% sucrose p.o.). Filled symbols are for results obtained with Cxc-BT, $5\times10^9$ cfu/100 $\mu$l i.p.

Antigen-specific antibody analysis of serum and intestinal (mucosal) secretions was performed using a solid phase enzyme-linked immunoabsorbant assay (ELISA). ELISA plates (eg. Immunolon 4, Dynatech) were coated with 100 μl/well of sonicated Cxc [10 μg/ml in PBS] (8 g/L NaCl, 0.2 g/L KCl, 1.15 g/L $Na_2HPO_4$, 0.2 g/L $KH_2PO_4$) or 10 μg/ml of BT (Ecogen Inc., Langhorne, Pa.) [prepared by heating BT crystals in an equal volume of 0.2M NaOH at 50° C., for 2 min overnight at room temperature (RT; about 25° C.). Coated plates were washed 3× with PBS-Tween (0.05%) and then blocked with 5% dried milk in PBS at RT for at least 1 hour. Sera or centrifuged [10 minutes at 1000 rpm] intestinal secretion preparations were added to the plates [30 μl/well] in various dilutions for 2 to 4 hours at RT. The plates were then washed 3× with PBS-Tween and peroxidase-conjugated secondary antibodies (either goat anti-mouse IgG whole molecule or goat anti-mouse IgA α-chain specific, or a mix of two), were added [100 μl/well at a final dilution of 1:5000 in PBS], for at least 1 hour at RT. Plates were then washed 5× with PBS-Tween and TMB (3, 3'5, 5' tetramethylbenzidine dihydrochloride, Signa) substrate added [100 μl/well] in phosphate-citrate buffer with urea for 30 min at RT in the dark. The reaction was stopped with 2M $H_2SO_4$ [50 μl/well] and the color change resulting from bound specific antibody measured at 450 nM in an ELISA plate-reader (Bio-Tek, Winooski Vt.). The results, expressed in O.D. units are shown in FIGS. 11 and 12.

Spleen T cells from Cxc-BT-fed mice were isolated and cultured with spleen antigen presenting cells as previously described (Hooper et al., PNAS 1994, 91:10908) with the exception that 10 μg/ml BT was employed as antigen. T cells were purified from single spleen cell suspensions by panning on petri plates coated with affinity purified goat anti-mouse Ig (eg. Rockland, Pa.). Purified splenic T cells and unselected spleen cells as APCs were cultured in a 1:1 ratio at a total of $2.5\times10^6$ cells/ml. The medium employed was Minimal Essential Medium Alpha Medium (alpha MEM) (Gibco Life Technologies Inc., Grand Island, N.Y.) supplemented with 4 mM L-glutamine (Gibco), gentamicin (Gibco), $5\times10^{-5}$M 2-mercaptoethanol (Sigma Chemical Co., St. Louis, Mo.), 20 mM HEPES (Gibco) and 0.6% fresh non-immune autologous normal mouse serum. Cultures were performed either in 200 μl volumes in 96 well round bottom microtitre plates or in 2 ml volumes in 24 well plates and were incubated at 37° C. in a humidified atmosphere of 5% $CO_2$ 95% air. Peak proliferative responses (72–96 hours of culture), measured by the incorporation of $^3$H-thymidine into newly synthesized DNA, are depicted in FIG. 13.

The amount of immunogenic response induced by the Cxc BT was surprising given the small amount of BT present (calculated to be approximately 2 to 3 nanograms) in the immunizing dose ($5\times10^7$ cfu) and given the fact that the few other processes using the oral immunization route tend to require massive doses of the order of milligrams for a comparable response.

Example 3

Immunization and Testing Protocol for N-transformed Cxc (Free of Plant Material)

Figure 14:
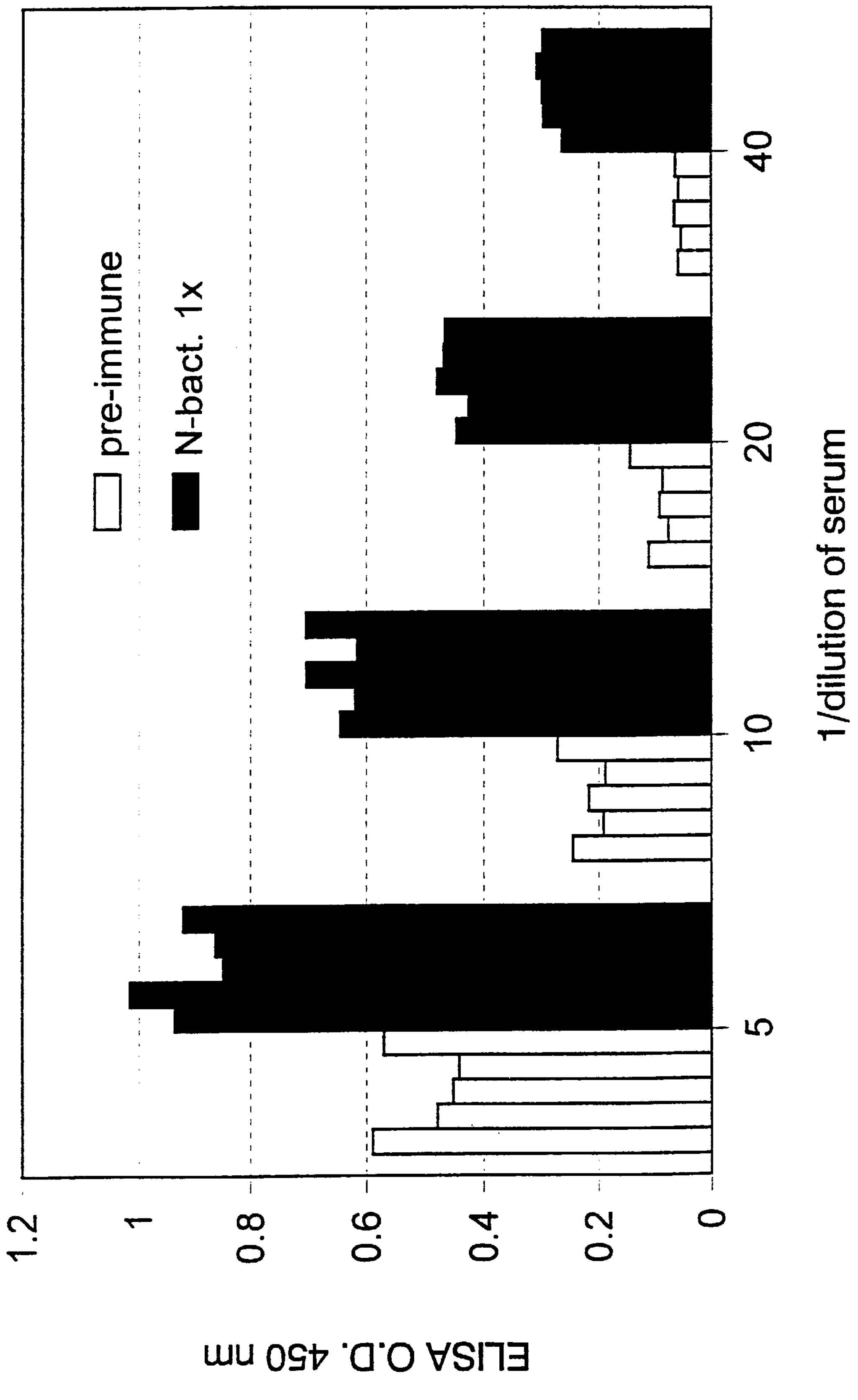
FIG. 14. Rabies nucleoprotein-specific IgG antibody elicited in serum by immunization with Cxc-N recombinant protein in CFA i.p.
Figure 15:
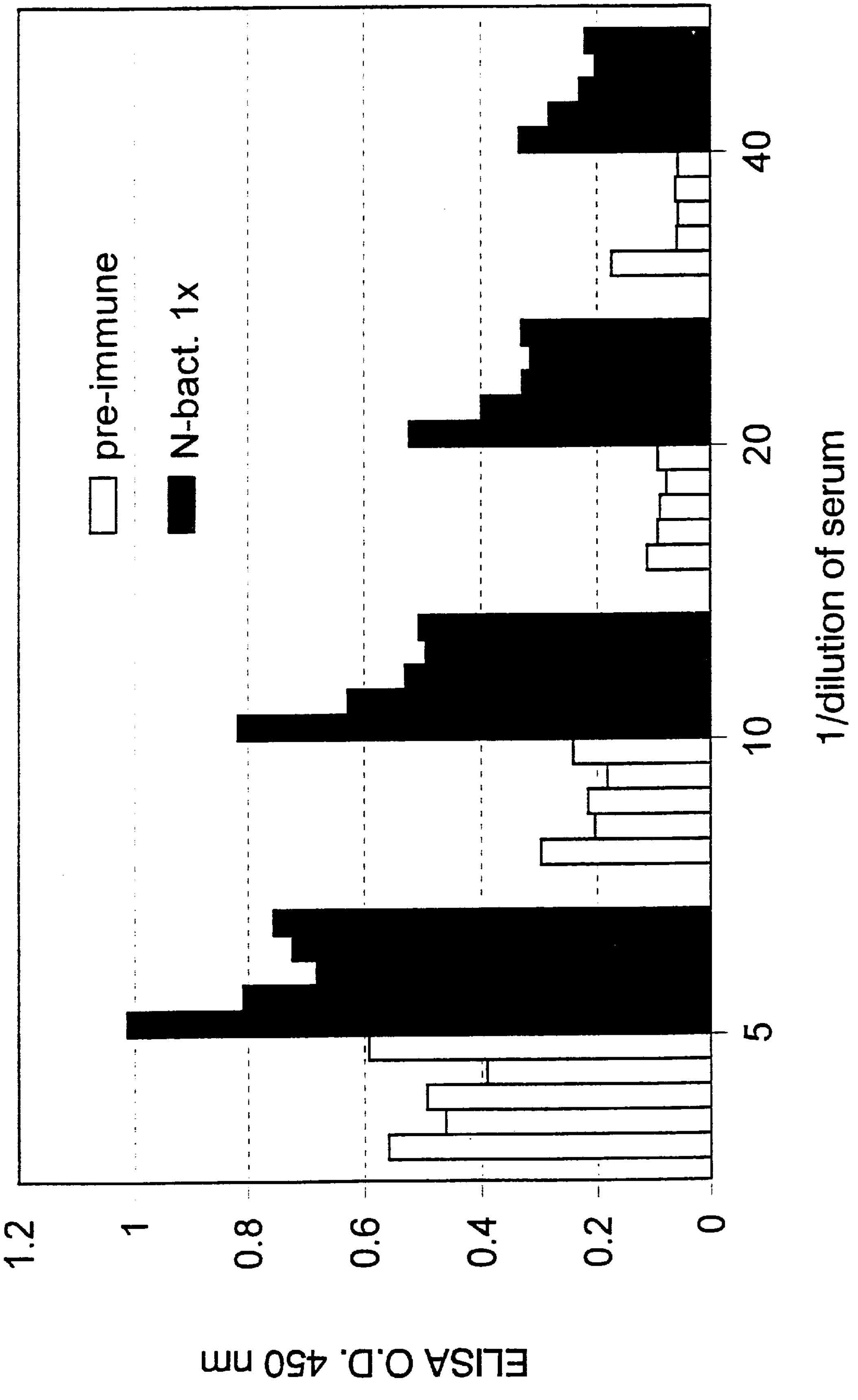
FIG. 15. Rabies nucleoprotein-specific IgG antibody elicited in serum by immunization with Cxc-N recombinant protein in saline i.p.

Cxc expressing the rabies nucleoprotein (the rabies "N protein") gene were injected i.p. ($5\times10^6$ in 100 μl PBS or 1:1 mix of PBS and CFA (complete Freund's adjuvant purchased from Gibco BRL.)) into adult Balb/c mice. Control mice were injected with 100 μl of PBS alone. Serum anti-N titers were determined in ELISA as in Example 2 except that rabies N protein was used as a target antigen instead of BT. Rabies N protein was prepared as described in Z. F. Fu et al, (1991) Proc. Nat'l Acad. Sci. USA 88: 2001–2005. Briefly, rabies N protein was purified by affinity purification from supernatants of Sf9 insect cells infected with recombinant baculovirus expressing N. The results of this experiment, which demonstrates that a single i.p. immunization with Cxc-N (Cxc expressing the N protein) is sufficient to elicit significant N-specific antibody titers are shown in FIGS. 14 and 15.

The effects of Cxc-N administration on immunity is further tested via other routes in a manner analogous to that described in Example 2. Groups of outbred and/or inbred C3H or Balb/c mice are given various doses of Cxc-N by different routes including gastric intubation, placement in the oropharynx, i.p. and i.m. injection. The latter are performed without, and with complete Freund's adjuvant. Per os administration is given 4 to 5 times at bi-weekly intervals while parenteral injection is given one to two times several weeks apart. Purified baculovirus-expressed rabies N protein is used as a control immunogen. Serum, intestinal secretions and lymphoid organs are harvested for assessment of humoral and T cell immunity as describe in Example 2 and Hooper et al., 1994. Target antigen for ELISA is either purified rabies N, rabies RNP (rabies ribonucleoprotein), or inactivated rabies virus. Protection experiments are performed with mice that have received Cxc-N with or without adjuvant in comparison with mice that have similarly received rabies N, rabies vaccine, or have been left untreated. The mice are infected with rabies street virus (50 $\mu$l/of coyote strain passaged 1× in neonatal brain, and then administered as a 1:30 neonatal mouse brain preparation) in the leg muscle. Serum is obtained by retro-orbital puncture and humoral responses to the immunization and infection are assessed by ELISA and neutralization assays prior to, and approximately 12–15 days after infection. The animals are examined for the development of clinical signs of rabies and for mortality. Animals that survive past 25 days after infection are euthanized, their serum again assessed for serum anti-rabies virus antibody titers and their brains analyzed for the presence of rabies virus antigens using fluorescein-conjugated antibodies specific for rabies N.

Example 4

Testing the Immune Status of Mice Following Oral Administration of Plants Infected with N-transformed Cxc Three groups of mice are fed: 1/ uninfected corn shoots and leaves; 2/ corn soots and leaves infected by seed infusion with wild-type Cxc; and 3/ corn shoots and leaves infected by seed infusion with Cxc expressing rabies virus N protein. An additional group of mice are left untreated. Mice are fed ad lib for 24 hours 4 to 5 times at 10 to 14 day intervals. Ten to 14 days following each feeding, approximately 5 mice from each group are utilized for test of systemic and mucosal immune responses to N protein as described in Examples 2 and 3 above. Protection experiments, as described in Example 3, are also carried out.

What is claimed is:

1. A process for synthesizing and delivering a polypeptide to a mammal, in order to induce an antibody or T cell response in said mammal, said method comprising the steps of:

1) genetically transforming a micoroorganism so that said transformed microorganism acquires the ability to synthesize said polypeptide, said microorganism being of the genus Clavibacter;

2) culturing the genetically transformed microorganism so that it synthesizes said polypeptide; and 3) administering the polypeptide synthesized during step (2) to a mammal via an oral route so that said polypeptide induces in said mammal an increase in the amount of antibodies against said polypeptide or the response of splenic T-cells to said polypeptide;

and wherein the culturing step, step (2) takes place in a plant.

2. A process of claim 1 wherein the microorganism is of the subspecies *Clavibacter xyli cynodotis.*

3. A process of claim 1 wherein in step (3) the polypeptide is in the genetically transformed microorganism but free of plant material.

4. A process of claim 1 wherein step (2) is accomplished in a plant after infection of the plant with the genetically transformed microorganism and in step (3) the polypeptide either is in the plant material derived from the plant used in step (2) or is in the genetically transformed microorganism in said plant material.

5. A process of claim 3 wherein the microorganism is of the subspecies *Clavibacter xyli cynodotis.*

6. A process of claim 4 wherein the microorganism of the subspecies *Clavibacter xyli cynodontis.*

7. A process of claim 1 wherein in the step (3) polypeptide is not free of plant material and genetically transformed microorganism material.

8. A process of claim 1 wherein the polypeptide is a viral polypeptide.

9. A process of claim 8 wherein the viral polypeptide is a rabies polypeptide.

10. A process of claim 3 wherein the polypeptide is a viral polypeptide.

11. A process of claim 10 wherein the viral polypeptide is a rabies polypeptide.

12. A process of claim 4 wherein the polypeptide is a viral polypeptide.

13. A process of claim 12 wherein the viral polypeptide is a rabies polypeptide.

14. A process of claim 1 wherein in step (3) the polypeptide is in the genetically transformed microorganism.

15. A process of claim 14 wherein before step (3) the polypeptide is isolated from plant material.

16. A process of claim 15 wherein the microorganism is of the subspecies *Clavibacter xyli cynodontis.*

17. A process of claim 7 wherein the polypeptide is a viral polypeptide.

18. A process of claim 17 wherein the viral polupeptide is a rabies polypeptide.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
(A) LENGTH: 27 base pairs
(B) TYPE: nucleic acid
(C) STRANDEDNESS: single
(D) TOPOLOGY: Linear (ii) MOLECULE TYPE:

(iii) HYPOTHETICAL: N (xi) SEQUENCE DESCRIPTION: SEQ ID NO:1:

CAGCACCCAT GGATGCCGAC AAGATTG 27

(2) INFORMATION FOR SEQ ID NO:2:

(i) SEQUENCE CHARACTERISTICS:
(A) LENGTH: 35 base pairs
(B) TYPE: nucleic acid
(C) STRANDEDNESS: single
(D) TOPOLOGY: Linear (ii) MOLECULE TYPE:

(iii) HYPOTHETICAL: N (xi) SEQUENCE DESCRIPTION: SEQ ID NO:2:

GCGAGAAGCT TGAATTCCTT CTTATGAGTC ACTCG 35

(2) INFORMATION FOR SEQ ID NO:3:

(i) SEQUENCE CHARACTERISTICS:
(A) LENGTH: 29 base pairs
(B) TYPE: nucleic acid
(C) STRANDEDNESS: single
(D) TOPOLOGY: Linear (ii) MOLECULE TYPE:

(iii) HYPOTHETICAL: N (xi) SEQUENCE DESCRIPTION: SEQ ID NO:3:

GCGAGCTCGA GCTTCTTATG AGTCACTCG 29

(2) INFORMATION FOR SEQ ID NO:4:

(i) SEQUENCE CHARACTERISTICS:
(A) LENGTH: 73 base pairs
(B) TYPE: nucleic acid
(C) STRANDEDNESS: double
(D) TOPOLOGY: Linear (ii) MOLECULE TYPE: Genomic DNA (iii) HYPOTHETICAL: N (xi) SEQUENCE DESCRIPTION: SEQ ID NO:4:

GGATCCGCTA CACGAGAGTC CTGAGGAGGA CCCACAGTGG 40

CTAAGGCCAA GTTCGAGCGG ACTAAGGCCA TGG 73

(2) INFORMATION FOR SEQ ID NO:5:

(i) SEQUENCE CHARACTERISTICS:
(A) LENGTH: 84 base pairs
(B) TYPE: nucleic acid
(C) STRANDEDNESS: double
(D) TOPOLOGY: Linear (ii) MOLECULE TYPE: Genomic DNA (iii) HYPOTHETICAL: N (xi) SEQUENCE DESCRIPTION: SEQ ID NO:5:

GGATCCGCTA CACGAGAGTC CTGAGGAGGA CCCACAGTGG 40

CTAAGGCCAA GTTCGAGCGG ACTAAGCAGG AGGCCTGACC 80

ATGG 84

(2) INFORMATION FOR SEQ ID NO:6:

(i) SEQUENCE CHARACTERISTICS:
(A) LENGTH: 27 base pairs
(B) TYPE: nucleic acid
(C) STRANDEDNESS: single
(D) TOPOLOGY: Linear (ii) MOLECULE TYPE:

(iii) HYPOTHETICAL: N (xi) SEQUENCE DESCRIPTION: SEQ ID NO:6:

CAGCACCCAT GGATGCCGAC AAGATTC 27

(2) INFORMATION FOR SEQ ID NO:7:

(i) SEQUENCE CHARACTERISTICS:
(A) LENGTH: 347 base pairs
(B) TYPE: nucleic acid
(C) STRANDEDNESS: double
(D) TOPOLOGY: Linear (ii) MOLECULE TYPE: Genomic DNA (iii) HYPOTHETICAL: N (xi) SEQUENCE DESCRIPTION: SEQ ID NO:7:

-continued

```
ATTCTGATCA GATCCGGAGT TCCGGCGAAG TCAACCTCGA          40

CACGCCCGGG TTGTCAGTCG AATTTGCACG CTCTCGGGGG          80

ACCTGCGTAA AGTACTTACT TGTCACCCCA AAGGTGCGGG         120

AGAGAGGAAG ATCTCCCCGG CCTCAAGTGG GACCAAGATC         160

CTTAGTTAGC GGCAATCTGA GCTTGTGAAA GTTCGTTTGT         200

ATCGCTTAGA ATAAATACCC CACTCACTGG ACAGGTCTAA         240

TCGCTTCGGA TCGCGAGCAG TCGGATGTAT CCCACGATGG         280

ATGAACGAAA AGCGCGAAAC GGACAGCTTG ACAAACTGAC         320

CGAGAGTGGT AAGATAGCGA AGGATCC                       347
```

(2) INFORMATION FOR SEQ ID NO:8:

(i) SEQUENCE CHARACTERISTICS:
(A) LENGTH: 1357 base pairs
(B) TYPE: nucleic acid
(C) STRANDEDNESS: double
(D) TOPOLOGY: Linear (ii) MOLECULE TYPE:

(iii) HYPOTHETICAL: N (xi) SEQUENCE DESCRIPTION: SEQ ID NO:8:

```
ATGGATGCCG ACAAGATTGT ATTCAAAGTC AATAATCAGG          40

TGGTCTCTTT GAAGCCTGAG ATTATCGTGG ATCAACATGA          80

GTACAAGTAC CCTGCCATCA AAGATTTGAA AAAGCCCTGT         120

ATAACCCTAG GAAAGGCTCC CGATTTAAAT AAAGCATACA         160

AGTCAGTTTT GTCAGGCATG AGCGCCGCCA AACTTGATCC         200

TGACGATGTA TGTTCCTATT TGGCAGCGGC AATGCAGTTT         240

TTTGAGGGGA CATGTCCGGA AGACTGGACC AGCTATGGAA         280

TCGTGATTGC ACGAAAAGGA GATAAGATCA CCCCAGGTTC         320

TCTGGTGGAG ATAAAACGTA CTGATGTAGA AGGGAATTGG         360

GCTCTGACAG GAGGCATGGA ACTGACAAGA GACCCCACTG         400

TCCCTGAGCA TGCGTCCTTA GTCGGTCTTC TCTTGAGTCT         440

GTATAGGTTG AGCAAAATAT CCGGGCAAAA CACTGGTAAC         480

TATAAGACAA ACATTGCAGA CAGGATAGAG CAGATTTTTG         520

AGACAGCCCC TTTTGTTAAA ATCGTGGAAC ACCATACTCT         560

AATGACAACT CACAAAATGT GTGCTAATTG GAGTACTATA         600

CCAAACTTCA GATTTTTGGC CGGAACCTAT GACATGTTTT         640

TCTCCCGGAT TGAGCATCTA TATTCAGCAA TCAGAGTGGG         680

CACAGTTGTC ACTGCTTATG AAGACTGTTC AGGACTGGTA         720

TCATTTACTG GGTTCATAAA ACAAATCAAT CTCACCGTTA         760

GAGAGGCAAT ACTATATTTC TTCCACAAGA ACTTTGAGGA         800

AGAGATAAGA AGAATGTTTG AGCCAGGCCA GGAGACAGCT         840

GTTCCTCACT CTTATTTCAT CCACTTCCGT TCACTAGGCT         880

TGAGTGGGAA ATCTCCTTAT TCATCAAATG CTGTTGGTCA         920

CGTGTTCAAT CTCATTCACT TTGTAGGATG CTATATGGGT         960
```

-continued

| | | | | |
|---|---|---|---|---|
| CAAGTCAGAT | CCCTAAATGC | AACGGTTATT | GCTGCATGTG | 1000 |
| CTCCTCATGA | AATGTCTGTT | CTAGGGGGCT | ATCTGGGAGA | 1040 |
| GGAATTCTTC | GGGAAAGGGA | CATTTGAAAG | AAGATTCTTC | 1080 |
| AGAGATGAGA | AAGAACTTCA | AGAATACGAG | GCGGCTGAAC | 1120 |
| TGACAAAGAC | TGACGTAGCA | CTGGCAGATG | ATGGAACTGT | 1160 |
| CAACTCTGAC | GACGAGGACT | ACTTCTCAGG | TGAAACCAGA | 1200 |
| AGTCCGGAGG | CTGTTTATAC | TCGAATCATG | ATGAATGGAG | 1240 |
| GTCGACTGAA | GAGATCTCAC | ATACGGAGAT | ATGTCTCAGT | 1280 |
| CAGTTCCAAT | CATCAAGCCC | GTCCAAACTC | ATTCGCCGAG | 1320 |
| TTTCTAAACA | AGACATATTC | GAGTGACTCA | TAAGAAG | 1357 |